US005520885A

United States Patent [19]
Coelho et al.

[11] Patent Number: 5,520,885
[45] Date of Patent: May 28, 1996

[54] FIBRINOGEN PROCESSING APPARATUS, METHOD AND CONTAINER

[75] Inventors: Philip H. Coelho; Terry Wolf, both of Rancho Cordova, Calif.

[73] Assignee: ThermoGenesis Corporation, Rancho Cordova, Calif.

[21] Appl. No.: 5,989

[22] Filed: Jan. 19, 1993

[51] Int. Cl.$^6$ ..................................................... B01L 7/00
[52] U.S. Cl. ........................... 422/101; 604/403; 530/427; 530/382; 422/255; 422/285
[58] Field of Search ................................. 62/56–57, 66, 62/68, 538, 342, 346; 604/113, 114, 403; 128/276; 530/427, 382; 210/787; 435/2; 422/255, 285, 99, 101

[56] References Cited

U.S. PATENT DOCUMENTS

| | | | |
|---|---|---|---|
| 2,543,808 | 3/1951 | Seegers et al. | 167/74 |
| 2,845,929 | 8/1958 | Strumia | 128/276 |
| 3,027,734 | 4/1962 | Mills | 62/375 |
| 3,492,991 | 2/1970 | Dyer, Jr. | 128/214 |
| 3,782,384 | 1/1974 | Timmermans | 128/277 |
| 3,920,625 | 11/1975 | Anderson et al. | 260/112 B |
| 3,928,566 | 12/1975 | Briggs et al. | 424/94 |
| 4,025,618 | 5/1977 | Garber et al. | 424/101 |
| 4,129,131 | 12/1978 | Naftulin | 128/276 |
| 4,141,887 | 2/1979 | Seufert | 260/112 B |
| 4,170,639 | 10/1979 | Liu et al. | 424/101 |
| 4,188,318 | 2/1980 | Shanbrom | 260/112 B |
| 4,322,275 | 3/1982 | Jain | 204/180 P |
| 4,416,772 | 11/1983 | Sato et al. | 210/137 |
| 4,503,039 | 3/1985 | Kotitschke et al. | 424/101 |

(List continued on next page.)

FOREIGN PATENT DOCUMENTS

| | | |
|---|---|---|
| 505962A1 | 9/1992 | European Pat. Off. . |
| 339896 | 8/1905 | France . |
| 1110542 | 2/1956 | France . |
| 2493178 | 7/1982 | France . |
| 62-180754 | 8/1987 | Japan . |
| 2014583 | 8/1979 | United Kingdom . |
| WO91/17641 | 11/1991 | WIPO . |

OTHER PUBLICATIONS

Carlebjork et al. New Frontiers in Hemophilia Research, Freezing of Plasma to Obtain Better Yield of Factor VIII:C, Scand J Haematol Suppl. 40, vol. 33, 1984, 127–128.
Lifesource Advanced BloodBank Systems 1990 Flash System & Related Products Catalog—entire catalog.

*Primary Examiner*—Michael G. Wityshyn
*Assistant Examiner*—Rachel Heather Freed
*Attorney, Agent, or Firm*—Bernhard Kreten

[57] ABSTRACT

An instrumentality for promulgating the cryoprecipitation of fibrinogen from a blood product. The instrumentality contemplates a container for the blood product, an apparatus for creating the fibrinogen within the container and a method of manipulating the container within the apparatus and subsequently after fibrinogen has been formed. The apparatus includes a receiver within which the container is supported, a motion transfer device for the receiver to impart motion to the container while simultaneously subjecting the container to a temperature differential to cause heat transfer. The motion imparted to the container results in a thin coating of the blood product being disposed on an interior surface of the container which, in turn, is exposed to a heat transfer fluid through the wall of the container. Successive coatings placed on an interior of the container are timed such that each coating is placed on a previous coating that has changed phase. Flexure of the container after the contents of the container have been frozen can occur by providing a vacuum within the container causing an implosion of frozen material. Subsequent phase change back to a liquid and then a second freeze/thaw followed by centrifugation causes a cryo-fraction to be precipitated therefrom. The container within which the blood product is housed includes an opening for admission of the blood product therewithin, an outlet for extraction of fibrinogen and access to a source which can provide a pressure differential vis a vis the interior and exterior of the container. Information of the temperature profile within the container may also be provided.

38 Claims, 11 Drawing Sheets

U.S. PATENT DOCUMENTS

| | | | |
|---|---|---|---|
| 4,627,879 | 12/1986 | Rose et al. | 106/124 |
| 4,638,048 | 1/1987 | Foster | 530/380 |
| 4,707,587 | 11/1987 | Greenblatt | 219/299 |
| 4,714,457 | 12/1987 | Alterbaum | 494/37 |
| 4,917,804 | 4/1990 | Franks et al. | 210/737 |
| 4,928,603 | 5/1990 | Rose et al. | 106/124 |
| 5,030,215 | 7/1991 | Morse et al. | 604/410 |
| 5,045,074 | 9/1991 | Satterfield et al. | 604/317 |
| 5,156,974 | 10/1992 | Grossman et al. | 436/69 |

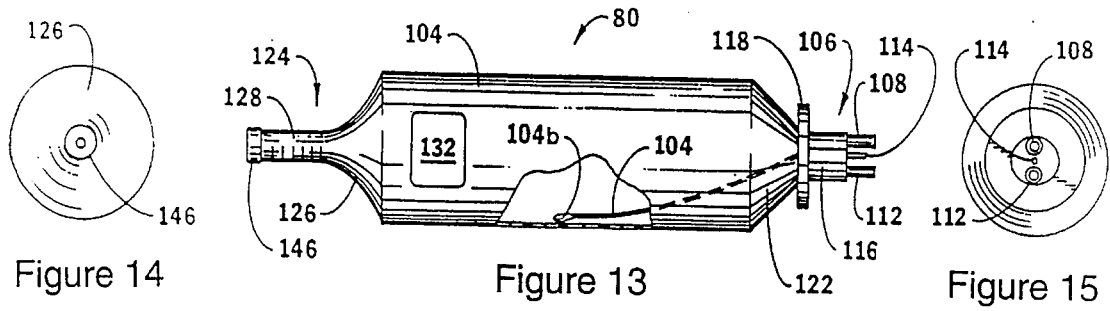
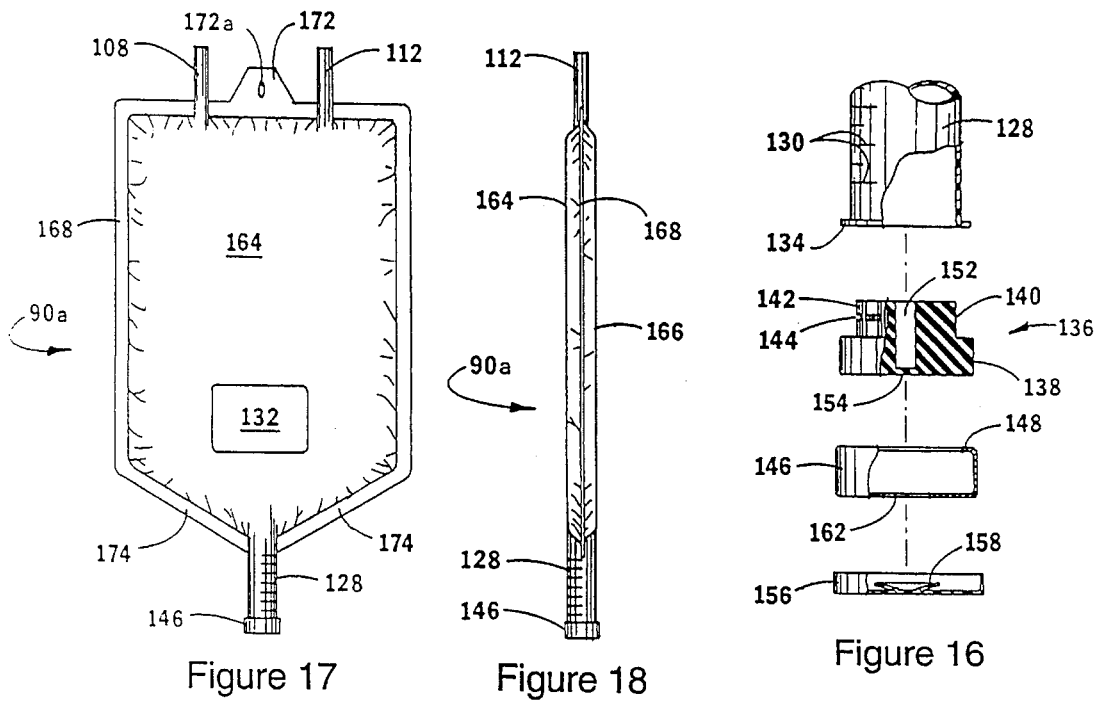
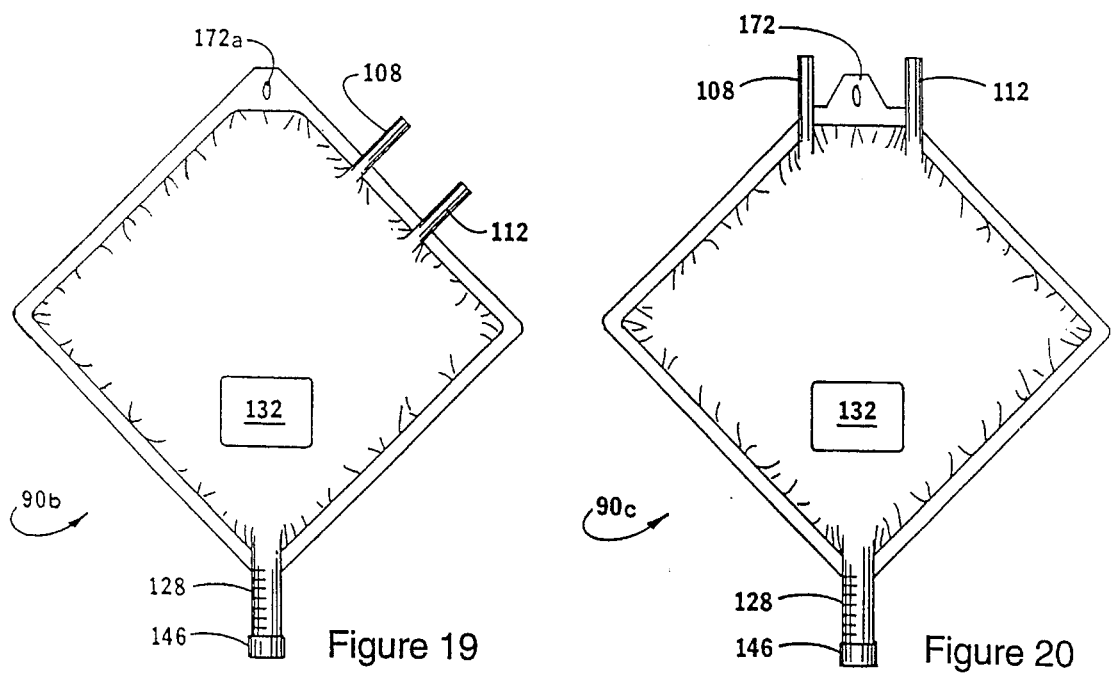

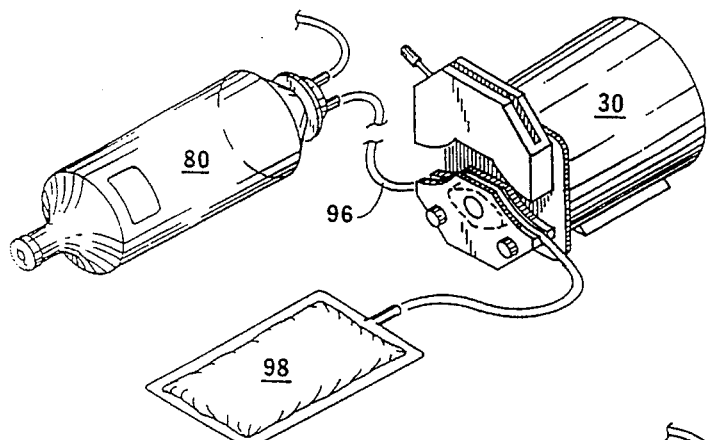
Figure 25
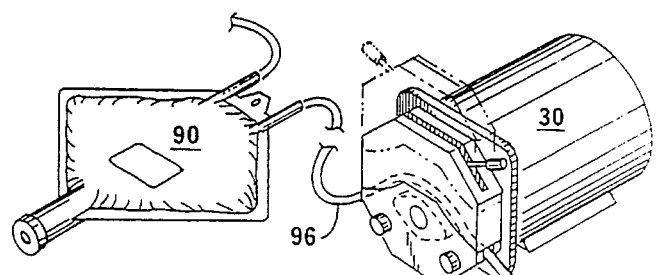
Figure 26
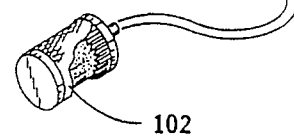
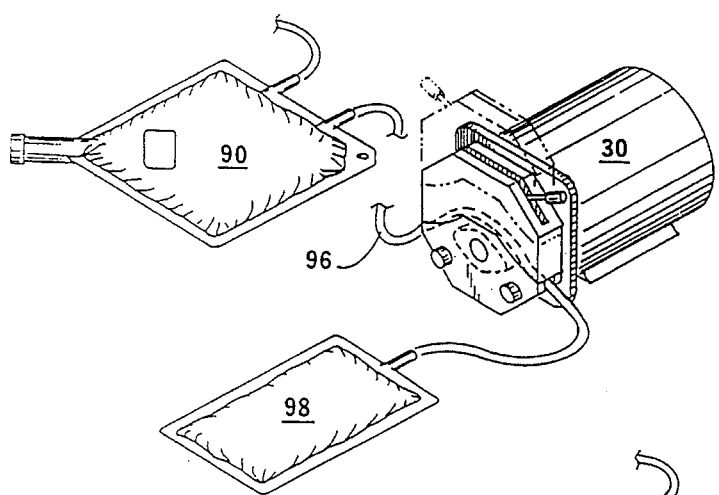
Figure 27
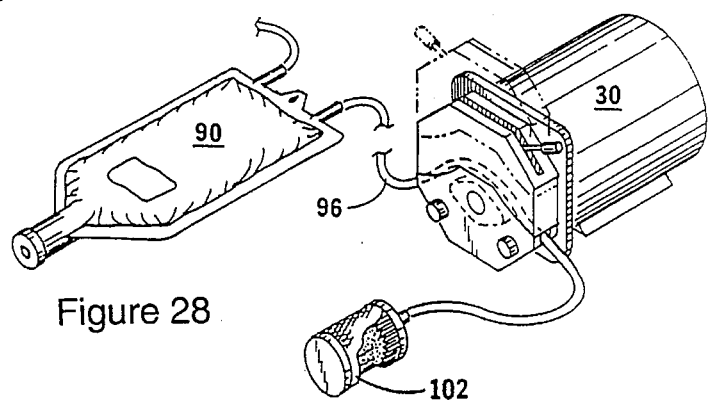
Figure 28

FIBRINOGEN PROCESSING APPARATUS, METHOD AND CONTAINER

FIELD OF THE INVENTION

The following invention relates generally to an apparatus, method and container for generating fibrinogen for use in a surgical environment.

BACKGROUND OF THE INVENTION

Sutures have been used as a conventional surgical means for uniting tissues and surgical margins, as hemostatic aids, and for blocking or ligation. However, sutures suffer from many drawbacks. For example, sutures may be incompatible with the tissue, causing fistula or granuloma, sutures may cut through parenchymal and inflammatory tissues, absorbable suture material may disintegrate prematurely and produce dehiscence of the wound, and closely spaced sutures may cause tissue ischemia resulting in necrosis of the wound margins. Suturing is also time-consuming.

In order to overcome the above-mentioned shortcomings of sutures, various attempts at developing suitable substitutes have been made. One goal has been the development of a tissue glue which ensures union of the tissue without causing any damage thereto.

Cyanoacrylate-based substances have been commonly used as a glue for tissue. However, these substances are toxic to the tissue and cannot be absorbed. As early as 1909, it was realized that "fibrin powder" could be utilized to achieve blood clotting and wound healing. Due to advances in basic research, it is now possible to prepare highly concentrated plasma products and isolate some coagulation factors.

In the human application, autologous plasma cryoprecipitate solution was first used, but since the clottable substances were found to be insufficient, homologous cryoprecipitate solution from pooled single-donor plasmas was subsequently used to obtain higher concentration for better tensile strength. Later, fibrin glue or sealant became more widely known.

Fibrin sealant has three components: fibrinogen concentrate, calcium chloride and thrombin. These components mimic the final common pathway of the clotting cascade, i.e. the conversion of fibrinogen to fibrin sealant.

In preparing fibrin sealant, thrombin of bovine or human origin is diluted with calcium chloride, with concentrations dependent on the tissue to be applied and the time of clotting. Equal amounts of fibrinogen concentrate and thrombin diluted in calcium chloride are used for clinical application. When the two components are mixed, thrombin converts fibrinogen to fibrin so that clotting is initiated and the mixture solidified. Meanwhile, in the presence of calcium ions, thrombin activates factor XIII to factor XIIIa. Activated factor XIIIa together with thrombin catalyzes the cross-linkage of fibrin and increases the strength of the clot. During wound healing the clot material undergoes gradual lysis and is completely absorbed. A major application of fibrin sealant is in surgery and in other areas of medicine.

Although there are great advantages to using fibrin sealant in clinical medicine, it is prohibited to use the commercially available product from pooled human plasma in the United States because of potential transmission of hepatitis B, acquired immunodeficiency syndrome (AIDS), and other transfusion transmittable diseases. The Food and Drug Administration (FDA) regulations have required that all plasma protein fractions shall receive heat treatment for not less than 10 or more than 11 hours at an attained temperature of 60°±0.5° C. to inactivate infectious agents.

Commercially available fibrinogen is prepared from the plasma pooling of a large number of donors, which has high potential for disease transmission. In addition, fibrinogen will not tolerate the ten hours of heating to 60° C. used to inactivate the hepatitis virus in other blood fractions. Studies have indicated that this product was a source of hepatitis transmission (7.8% of post-transfusion hepatitis rate). Under these circumstances, the FDA revoked all licenses for the manufacture of human fibrinogen since Jun. 30, 1978.

In Europe, fibrinogen product is commercially available as a fibrinogen concentrate kit ("Tisseel", Immonu AG, Vienna, Austria) prepared from pooled fresh frozen plasma. The tensile strength for Tisseel is 900 /g/cm$^2$. Since this commercial fibrinogen concentrate is not available in the United States because it is currently not licensed by the FDA, alternative methods such as chemical precipitation and cryoprecipitation have been used to prepare fibrinogen concentrate.

Fibrinogen is one of the three main protein constituents of plasma. The major constituent, albumin (ALB), occurs in a concentration of approximately four percent. The plasma globulins are present in a concentration of about 2.5 percent and are particularly associated with-the processes of immunity. Fibrinogen occurs in much smaller amounts, with its concentration in human plasma being about 0.4 percent.

Several authors have discussed fibrinogen/fibrinogen interaction and fibrinogen interaction with other proteins. Aggregation of fibrinogen at pH 5.7 and low ionic strength (<0.3) has been found. A disulfide bond between fibrinogen molecules in cold-insoluble fibrinogen fraction has been demonstrated. It has been thought that the cold-insoluble precipitate that formed from normal plasma was a reaction between cold-insoluble globulin (CIg), fibrinogen and fibrin.

The plasma proteins can be separately isolated by: 1) organic solvents such as methanol or ethanol at low temperature using Cohn's fractionation, 2) cryoprecipitation, 3) chemical precipitation of plasma with salts such as ammonium sulfate, potassium phosphate, and sodium citrate, and 4) other methods. The solubility of the plasma proteins in these substances decreases in the order of albumin, globulin, and fibrinogen. The latter precipitates first and albumin last upon the addition of increasing amount of the precipitating agent.

1. Ethanol Fractionation (Cohn's fractionation)

In this process, 1,000 to 1,500 liters of 4,000–6,000 human source plasma are pooled and treated sequentially in the cold with various concentrations of ethanol and buffers to precipitate fractions containing different plasma proteins. Fibrinogen is the first material precipitated and harvested at −5° C. with 25% ethanol at a pH of 6.9. Variables determining the precipitation of proteins are ethanol concentration, pH, temperature, ionic strength and protein concentration.

2. Cryoprecipitation

The standard cryoprecipitation method has been primarily used to prepare antihemophilic factor (Factor VIII). Cryoprecipitate also has been known as a source of fibrinogen. The cryoprecipitate method can be also used to prepare fibrinogen concentrate. It is known that some factors might affect the yield of Factor VIII, such as ABO blood grouping, freezing and thawing conditions. With respect to Factor VIII preparation, others have studied freezing and thawing conditions (see Brown, et al., "Antihaemophilic Globulin: Preparation by an Improved Cryoprecipitation Method and Clinical Use", Br Med J 2, 79–85, 1967). However, all the factors for cryoprecipitation are not known.

It has been observed that when frozen plasma is thawed in the cold at 4° C., most of the Factor VIII remains in the cold-insoluble precipitate. This precipitate also contains variable amounts of fibrinogen ranging from 100 to 300 mg/single donor unit of cryoprecipitate. It has become routine to prepare anti-hemophilic factor (Factor VIII) and fibrinogen using the cryoprecipitation method in the blood bank using a closed system of plastic bags to maintain the sterility of the product from collection of the whole blood from the donor.

3. Chemical Precipitation

Human fibrinogen can be precipitated from human plasma by ammonium sulfate, polyethylene glycol, plyvinyl-pyrrolidone, and barium/magnesium sulfate. Entering the closed blood bag system for the addition of chemicals opens the system to the potential for bacterial contamination. Small amounts of fibrinogen concentrate solution (0.5–1.9 ml) can be prepared using these methods, but the side effects and safety due to the chemical substances as well as bacterial contamination opportunities are of great concern.

4. Other Methods

Sporadic reports have mentioned the use of the following methods to prepare purified fibrinogen: chromatography, polyelectrolyte fraction technology, recombinant DNA technology and ion exchange chromatography.

Fibrinogen concentrate can be prepared from random single-donor fresh frozen plasma or autologous plasma in sufficient quantity to meet some surgical demand. According to the Standards of the American Association of Blood Banks, fibrinogen concentrate can be currently stored for up to 5 years at −80° C. or at least 5 days at 4° C. until it is needed. Cryoprecipitate contains Factor VIII and fibrinogen and is used to supply fibrinogen in patients with hypofibrinogemia and also as an alternative source of fibrinogen concentrate for fibrin sealant in the United States.

However, traditional cryoprecipitation suffers from problems including the recovery of only small amounts of fibrinogen having low tensile strength when using single-donor cryoprecipitate to prepare fibrin sealant. Further, the fibrinogen concentrates prepared by traditional cryoprecipitation have a concentration range of 260–2,500 mg/dl. This is not an adequate concentration for applying this product as a tissue sealant over highly vascular areas. High fibrinolytic activity over that area breaks down the fibrin clot very quickly. These concentrates have a tensile strength of around 120 gm/cm$^2$ which is usually not sufficient for surgical applications.

The following patents reflect the state of the art of which applicant is aware insofar as these patents appear germane to the patent process. However, it is respectfully stipulated that none of these patents teach singly nor render obvious when considered in any conceivable combination the nexus of the instant invention as set forth hereinafter.

| INVENTOR | PATENT NO. | ISSUE DATE |
| --- | --- | --- |
| Seegers, et al. | 2,543,808 | 1951 |
| Strumia | 2,845,929 | 1958 |
| Mills | 3,027,734 | 1962 |
| Dyer, Jr. | 3,492,991 | 1970 |
| Timmermans | 3,782,384 | 1974 |
| Anderson, et al. | 3,920,625 | 1975 |
| Briggs, et al. | 3,928,566 | 1975 |

-continued

| INVENTOR | PATENT NO. | ISSUE DATE |
| --- | --- | --- |
| Garber, et al. | 4,025,618 | 1977 |
| Naftulin | 4,129,131 | 1978 |
| Seufert | 4,141,887 | 1979 |
| Pritchard | 2,014,583 (UK) | 1979 |
| Liu, et al. | 4,170,639 | 1979 |
| Shanbrom | 4,188,318 | 1980 |
| Jain | 4,322,275 | 1982 |
| Sato, et al. | 4,416,772 | 1983 |
| Kotitschke, et al. | 4,503,039 | 1985 |
| Rose, et al. | 4,627,879 | 1986 |
| (Japan) | 62-180754 | 1987 |
| Foster | 4,638,048 | 1987 |
| Greenblatt | 4,707,587 | 1987 |
| Alterbaum | 4,714,457 | 1987 |
| Franks, et al. | 4,917,804 | 1990 |
| Rose, et al. | 4,928,603 | 1990 |
| Morse, et al. | 5,030,215 | 1991 |
| Satterfield, et al. | 5,045,074 | 1991 |
| Harms, et al. | WO 91,17641 & Catalogue | 1991 |
| Grossman, et al. | 5,156,974 | 1992 |

OTHER PRIOR ART (Including Author, Title, Date, Pertinent Pages, Etc.)

Lifesource Advanced BloodBank Systems 1990 Flash System and Related Products Catalog, entire catalog None of the prior art resolves the longstanding and vexing problem that is manifested by the inefficient extraction of fibrinogen. Optimization of fibrinogen extraction particularly as outlined hereinafter, makes possible autologous generation of fibrinogen from an individual substantially contemporaneously with surgery such that the fibrinogen is extracted from the patient and the residual blood components are restored to the individual with no discernable adverse effects that would mitigate against proceeding or continuing with the operation.

SUMMARY OF THE INVENTION

The instant invention is distinguished over the known prior art in a multiplicity of ways. Conceptually, the instant invention is starkly quicker in the formation of fibrinogen partly by changing the manner in which the problems of heat transfer have been addressed. By changing the traditional heat transfer geometry in fibrinogen precipitation, improvements have been made over the prior art.

Heretofore, the accepted parameters for subsequent cryoprocessing typically involved treatment of blood products contained in a pouch. The instant invention changes the geometry of the blood product by housing it within a container so that greater surface area beneficially accelerates the cryoprecipitation effect. Generally, heat transfer through liquids is quicker than through a gas. The instant invention strives to provide liquid to liquid contact during the phase when the blood product is frozen and subsequently when it is being thawed. The freezing process involves primarily only thin coatings of the blood product. This is achieved by coating an interior of a container within which the blood product is contained through motion of the container with respect to the blood product. Spraying heat transfer fluid on an exterior of the container and over these coated areas will cause the coating to change phase rapidly while liquid still remains within the container. Subsequent motion of the liquid within the container will cause a new coating to be formed on top of a previously frozen layer. In the presence of additional heat transfer fluid, successive thin coatings will freeze in a fraction of the time than would normally occur without using the thin film coating process described herein.

Various mechanisms are contemplated to provide the thin film on walls of the container to facilitate the heat transfer process. In general, a periodic, oscillatory motion is preferred which is synchronized to the rate at which the thin coating changes phase from a liquid to a solid. More specifically, a rotary motion which rotates a substantially cylindrical object about its long axis is preferred such that the rotation occurs through an arc of a circle and then repeats itself at the appropriate rate to promulgate successive thin coatings to change from a liquid to a solid. In another form of the invention, the container within which the liquid is housed is a bag. The bag is deformed to be a substantially hollow annulus. Heat transfer can then occur through coating both interior cylindrical surfaces of the annulus. Heat transfer fluid can be sprayed on all exterior cylindrical surfaces of the annular container.

After the liquid has changed phase and frozen to a solid, the next phase of the process begins. The freezing spray is halted and a heat transfer coolant which is warmer than the freezing point of the frozen plasma is then sprayed on the exterior surface of the container. Soon after the warm spray has raised the temperature of the container to a temperature range wherein the container material is flexible and the thawing of the frozen plasma has begun, a vacuum is applied to the interior of the container. It is preferred that the container be formed from a class of materials, geometry and construction so that some degree of wall flexure in the presence of the vacuum is possible without compromising the sterile integrity of the container. By deforming the walls of the container, the somewhat brittle, solid blood product which has been frozen into a thin cylindrical shell collapses into pulverulent material. The purpose of converting the frozen plasma cylindrical shell into many smaller pieces is to significantly increase the surface area of the plasma particles in order to serve two purposes. First, the increased surface area of the plasma particles allows accelerated heat absorption from the melted liquid plasma which is washing back and forth intermixed with the shrinking frozen particles of plasma in the container. Second, the greater surface area of the frozen plasma particles tends to "clamp" the temperature of the melted plasma close to the approximate 0° C. freezing point of the frozen plasma thereby preventing an uncontrollably fast increase in temperature of the melted plasma to a point greater than 4° C. where the fibrinogen would resolubilize. This temperature clamping allows a greater temperature of the heat transfer fluid to be used without having the plasma exceed the critical 4° C. temperature. Consequently an accelerated thawing rate can be achieved.

Once this thawing process is completed it is possible to centrifuge out dense material at this stage. However, a preferred form of the invention entails a second refreezing step as described above followed by a successive thawing step described as above and finally centrifuging.

The foregoing process results in cryo-stratification wherein the fibrinogen will have been centrifuged to a bottommost portion of the container and accessible for extraction therefrom. In a preferred form of the invention, direct access to the centrifuged bottom portion containing the fibrinogen is contemplated so that it may be drawn from the container separate from the lighter fraction which has not precipitated. The lower fraction containing the fibrinogen is allowed to resolubilize so that it can be easily drawn into a syringe, but the container is held in a fixed position to still maintain the stratification.

One technique for maximizing the extraction of fibrinogen from the container involves providing a lowermost portion of the container with a series of gradations which denote the harvested fraction of the fibrinogen. The fibrinogen fraction is visually discernable prior to resolubalizing. This quantum is recorded so that upon resolubization of the fibrinogen, only that exact same amount can be extracted from a container bottom having a valved, sealed portion for use in increments which may be less than the total fraction available. It is to be noted that, after centrifugation, if left undisturbed the fibrinogen will remain at the bottom of the container.

OBJECTS OF THE INVENTION

Accordingly, it is a primary object of the present invention to provide a novel and useful method, apparatus and container for the expeditious cryoprecipitation of fibrinogen from a blood product.

It is another object of this invention to provide an instrumentality as characterized above which more completely extracts the fibrinogen component from a blood product than has been heretofore available, and to do so within a time frame that makes it possible to create the fibrinogen substantially contemporaneously with its use. Heretofore, fibrinogen which was derived from an autologous source, needed to be prepared well in advance of an operatory procedure. It is now possible with the teachings associated with this invention to utilize the quick fibrinogen making potential simultaneously during surgery as well as prior to surgery. It should be noted that standard practice during surgery involves recirculating the blood which normally develops through a series of conditioning devices for transfusing into the patient. This technique substantially reduces or even eliminates the need for blood from another source. With the structure according to the instant invention, the potential exists for diverting a portion of the patient's blood during the operation in order to form the fibrinogen and return the non-precipitated fraction back to the patient.

It is a further object of the present invention to provide an instrumentality as characterized above which is durable in construction, relatively easy to use, and achieves a cost of production of fibrinogen that can compete with costs resulting from the economies of scale associated with mass production techniques.

A further object of the present invention contemplates providing an instrumentality as characterized above in which a thin coating of the blood product is placed on interior walls of a container which houses the blood product. The container exterior is simultaneously exposed to a temperature gradient by fluid contact coupled with an oscillatory coating rate that matches the rate at which a change of phase occurs of the liquid being coated on an interior of the container. An iterative series of coatings on the container interior will therefore change phase substantially instantaneously. This rapidly accelerates the change of phase process because the thin coating step increases the surface area for heat transfer.

Viewed from a first vantage point, it is a further object of the present invention to provide a method for changing the phase of a fluid, the steps comprising placing the fluid in a container such that not all of the container has the fluid therein, coating an interior wall of the container with a thin film of the fluid, and exposing a corresponding exterior wall of the container to a first heat transfer medium such that heat transfer proceeds through the wall of the container affecting the thin film of the fluid by causing a first change of phase in the fluid film.

Viewed from a second vantage point, it is a further object of the present invention to provide an apparatus for extracting fibrinogen from a blood product, comprising in combination a container for the blood product having sufficient volume to include ullage within said container, a container support for removeably securing said container to said apparatus, means to move said container operatively coupled to said container support so that a thin film of the blood product coats an interior of the container, and temperature gradient means juxtaposed proximate an exterior of said container to alter the temperature profile of the blood product by thermal exchange through the container and to the thin film as it coats said container during container motion.

Viewed from a third vantage point, it is a further object of the present invention to provide a container for fractionating fluids, comprising in combination a closed wall construct defining said container, an inlet passing into said container for transferring the fluid from a remote source to an interior of said container, a vent passageway passing into said container for providing and maintaining a change in the internal pressure of said container, and a fractionate outlet passing through said container to facilitate the egress of fractionable material therefrom.

These and other objects will be made manifest when considering the following detailed specification when taken in conjunction with the appended drawing figures.

BRIEF DESCRIPTION OF THE DRAWING FIGURES

FIG. 13 is a side view of the container in one form of the invention.

FIG. 14 is an end view thereof.

FIG. 15 is an opposite end view of that which is shown in FIG. 14.

FIG. 16 is an exploded parts view, partially in section of the FIG. 14 end.

FIG. 17 is an embodiment which is an alternative to that which is shown in FIG. 13.

FIG. 18 is a side view of that which is shown in FIG. 17.

FIG. 19 is another alternative to that which is shown in FIGS. 13 and 17.

FIG. 20 is another variant of that which is shown in FIG. 19.

FIG. 25 shows the container according to the first form of the invention in operative communication with a source of sterile air.

FIG. 26 is a view similar to FIG. 25 showing a different container and a different air source.

FIG. 27 is a view similar to FIG. 26 showing a different container and the similar air source of FIG. 25.

FIG. 28 is a view similar to FIG. 27 showing a different container and the same air source as in FIG. 26.

DESCRIPTION OF PREFERRED EMBODIMENTS

Figure 1:
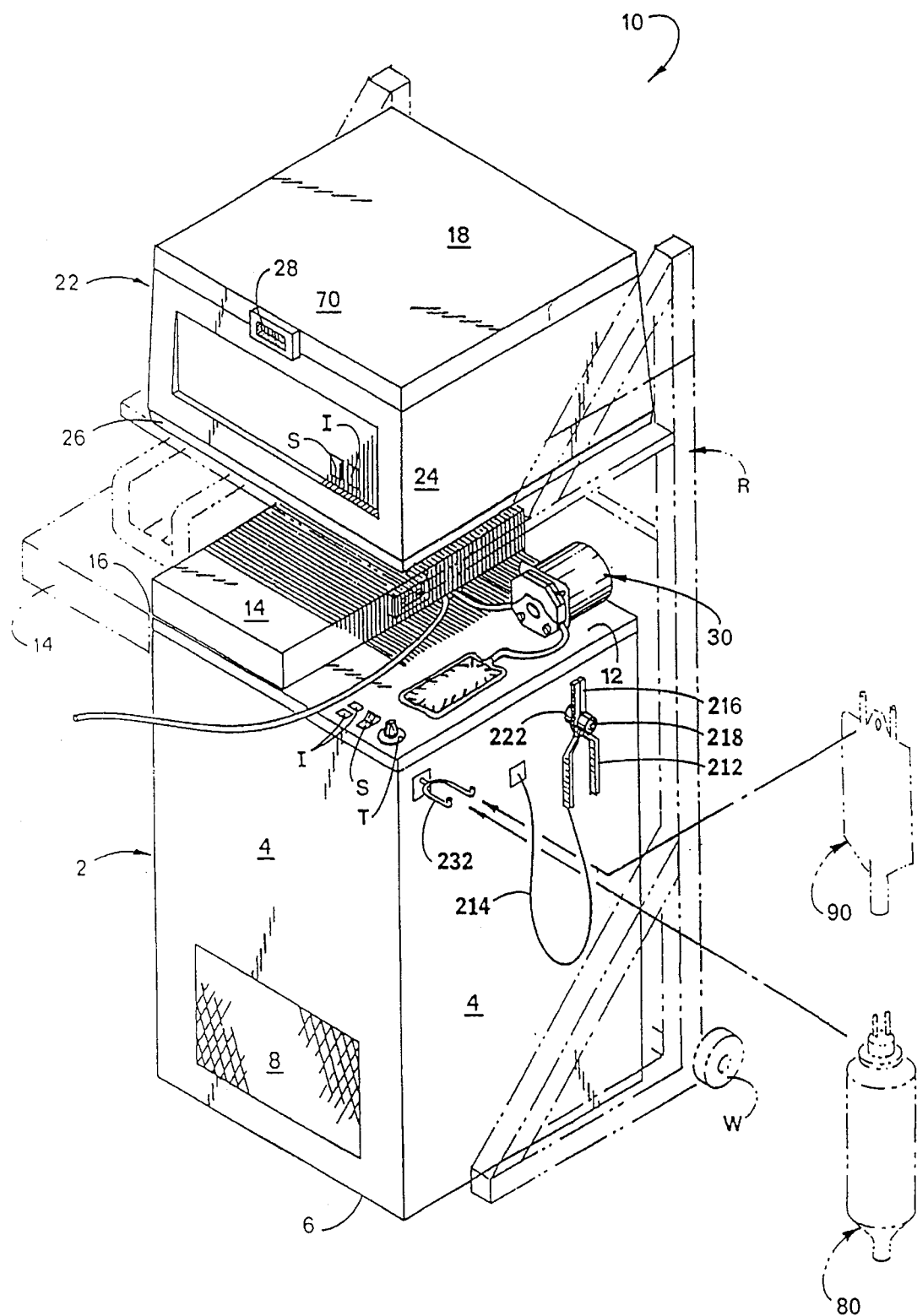
FIG. 1 is perspective of the exterior of the apparatus according to the present invention.

Considering the drawing now, wherein like reference numerals denote like parts throughout, reference numeral 10 of FIG. 1 is directed to the apparatus for cryoprecipitating fibrinogen from a blood product according to the present invention. Reference numeral 80 is directed to a container according to one form of the invention and reference numeral 90 is generally directed to another form of container.

Figure 2:
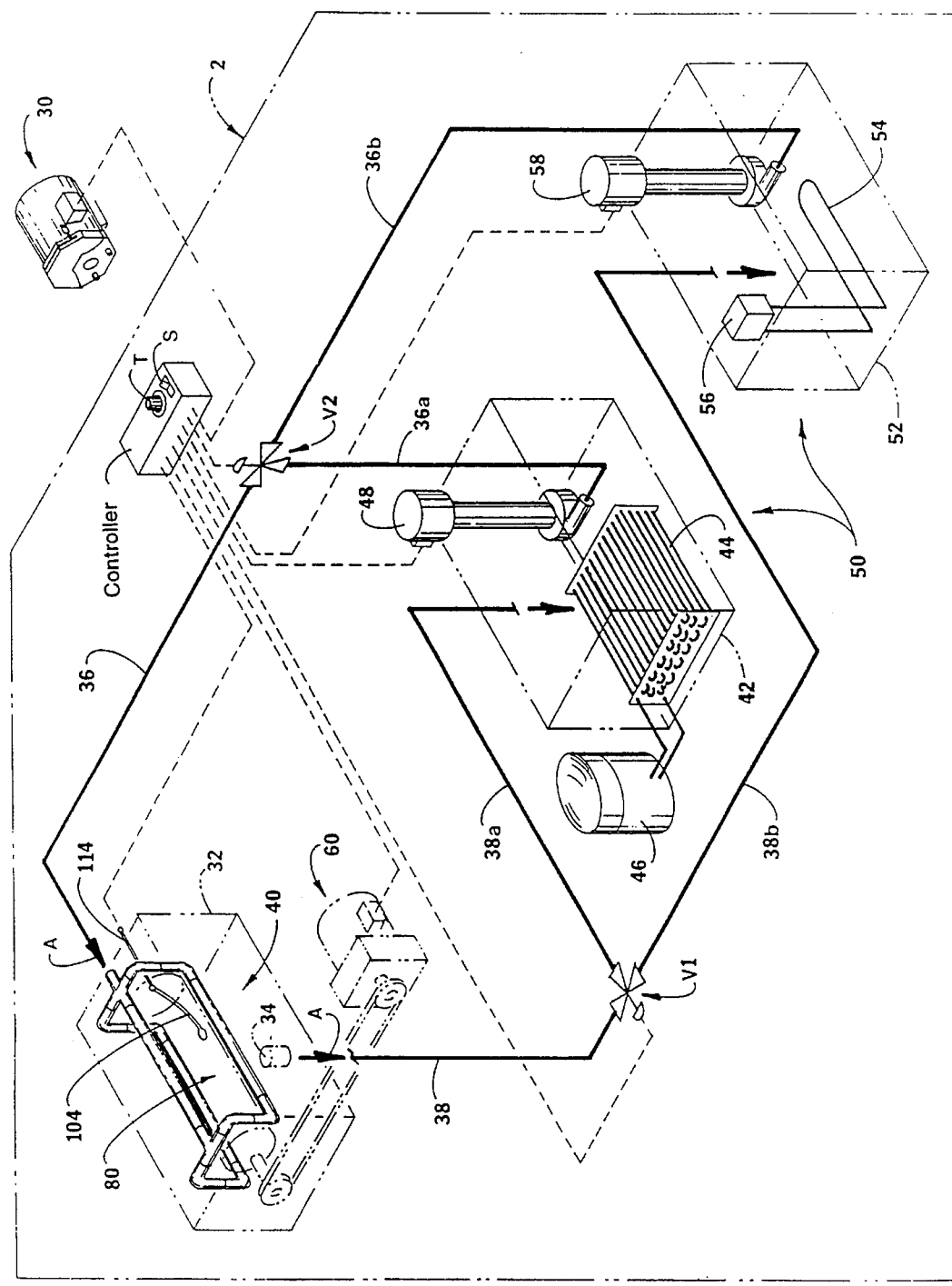
FIG. 2 is a schematic depiction of an interior plumbing system of the apparatus shown in FIG. 1 showing first and second heat transfer storage tanks in operative communication with a spray station.

In essence and viewing FIGS. 1 and 2, the apparatus 10 includes a receiver 20 for constraining the container therewithin during the fibrinogen formation process, a fluid delivery system 40 which communicates with a fluid reservoir system 50 and appropriate plumbing associated therewith. A means 60 for imparting motion allows the receiver 20 to rotate the containers 80 or 90. Finally, a centrifuge 70 helps in the formation of the cryoprecipitate.

More specifically, the apparatus 10 shown in FIG. 1 includes a rack R shown in phantom for reliably supporting several of the components that define the invention. The rack R could be equipped with wheels W should it be desired to transport the apparatus 10 from one location to another. The rack R in this event is configured somewhat like a hand truck or dolly in which first and second spaced, parallel vertically upstanding members each form the top leg of two L-shaped brackets having a horizontal leg adjacent a lowermost portion of the apparatus 10. The wheel W is supported by an axle attached near the intersection of vertical and horizontal legs which form the L-shaped bracket. A diagonal brace can extend between the vertical and horizontal legs of the L-shaped bracket. In addition, a shelf is provided and supported at an uppermost portion of each vertical leg. The shelf may similarly be provided with diagonal braces for supporting the centrifuge 70 on the shelf. A horizontal hand rail is medially disposed along the length of the vertical legs of the L-shaped bracket. The hand rail is oriented parallel to a lower brace which is also located between the two L-shaped brackets adjacent the wheels W. The hand rail and brace facilitate rocking the cart backwards to support it on the wheels W for transport.

The housing of the apparatus 10 includes a lower carton 2 and an upper box 22. More specifically, the lower carton 2 includes a plurality of upwardly extending side walls 4 overlying a bottom wall 6 to define an open topped carton. A front side wall is provided with a vent grill 8 so that the machinery contained within the lower carton can breath properly. The carton 2 includes a top wall 12 which occludes the access to the interior. A door 14 is supported on a marginal edge between the top wall 12 and one side wall 4 by means of a hinge 16 so that the door 14 can move from a first position in FIG. 1 to a second position (shown in phantom). The top wall 12 of the carton 2 also includes a plurality of indicator lights I showing status within the interior of the carton 2, a power switch S and a timer T for purposes to be assigned. In addition, an upper surface of the top wall 12 also supports a pump 30 having a purpose which will become evident in the ensuing description.

The housing also includes an upper box 22 within which the centrifuge 70 is stored. Essentially, the upper box 22 includes another open top structure having a lid 18 revealing access to an interior defined by four vertically oriented panels defining side panels 24 and a bottom panel 26. A latch mechanism 28 secures the lid 18. A front surface of one side panel 24 includes a power switch S and an indicator light I for purposes to be assigned.

Attention is now directed to FIG. 2 which delineates certain attributes contained within the lower carton 2. As mentioned above, a reservoir system 50 communicates with the fluid delivery system 40 in a manner to now be defined. The fluid delivery system 40 is mounted on an inner surface of the door 14 so that rotation of the hinge allows the door 14 to go from an open position to a closed position. FIG. 2 shows the fluid delivery system 40 when the door 14 is in the closed position and the fluid delivery system 40 addresses a container e.g. 80 which is nested within a fluid receiving well 32.

The well 32 includes a drain 34 so that fluid passing through the fluid delivery system 40 is captured by the well and recycled via the drain. Preferably, the well 32 is an open top construct with the bottom wall suitably canted to catch and redirect all liquid coming from an inlet conduit 36 through the drain 34 and into an outlet conduit 38. The outlet conduit 38 can communicate with one of two branch passageways: a first branch outlet conduit 38a which communicates with a refrigeration well 42 and a second outlet conduit branch 38b which communicates with a heat well 52. Valve V1 communicates the outlet conduit 38 to either the outlet refrigeration branch 38a or the outlet heat branch 38b via means not shown in FIG. 2, but to be described in greater detail hereinafter.

Fluid passing through refrigeration branch 38a is deposited into the refrigeration well 42 which is configured as an enclosed volume having a cooling coil 44 which is maintained in a cold condition by means of a condenser 46. When refrigeration fluid contained within the well is needed, it is delivered to the inlet conduit 36 by means of a pump 48 which has an inlet in fluid communication with the refrigeration well and an outlet that communicates with the inlet conduit 36 by means of inlet refrigeration branch 36a.

Similarly, the heat well 52 receives fluid from the heat outlet branch 38b where its temperature will be restored by means of a heating element 54 powered by an electrical source 56 so that the fluid contained therein is delivered at an optimal temperature. An inlet heat branch 36b delivers heated fluid from the heat well 52 to the inlet conduit 36 under pressure by means of a pump 58. Both inlet branches 36a and 36b communicate with the inlet conduit 36 selectively by means of a valve structure V2 shown schematically and adapted to operate in concert with valve V1 in a manner to be described. Thus, as shown in FIG. 2, the flow of fluid circulation as suggested by the arrows "A" immediately adjacent the well 32 occurs in a counterclockwise direction.

Figures 3, 3A:
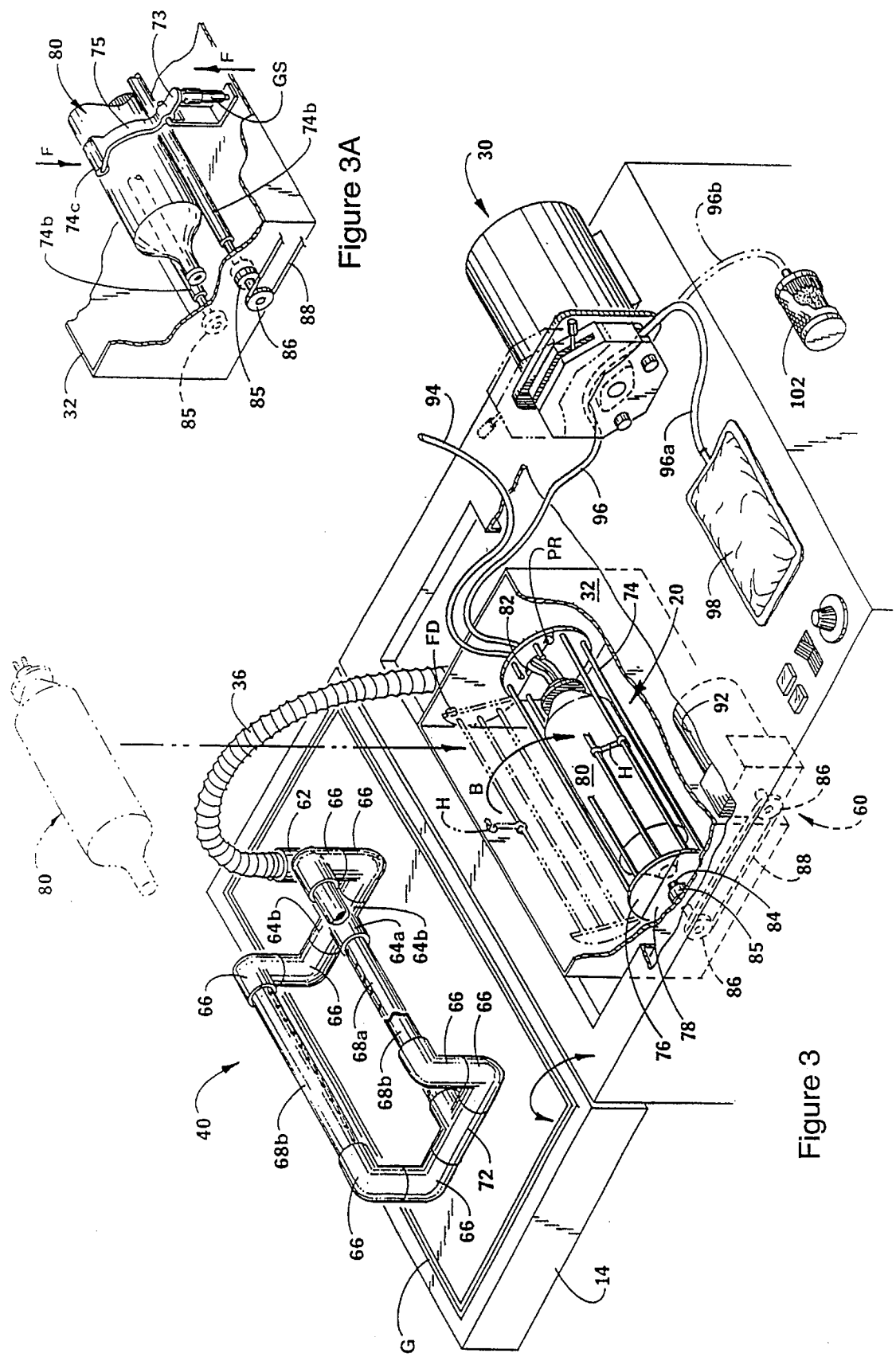
FIG. 3 is a perspective view of details of the spray station and its cooperation with a retainer mechanism for a container, associated with a pumping device.
FIG. 3A is an alternative embodiment of the retainer mechanism shown in FIG. 3.

FIG. 3 reflects certain details with respect to the fluid delivery system 40 which functions as a spray station for coating an exterior surface of the container 80 or 90. More specifically, FIG. 3 shows the inlet conduit 36 where it communicates with the fluid delivery system. Conduit 36 is formed as a flexible pipe which coacts with a manifold style fluid delivery system formed from rigid material, such as PVC piping. The system 40 is affixed to a bottom surface of the door 14. The flexible inlet conduit 36 permits the door 14 to open and close even though the fluid delivery system 40 is attached to the door.

In essence, the fluid delivery system 40 is oriented to circumscribe a top and side surfaces of the container 80 to ensconce the container in heat transfer fluid. The heat transfer fluid is preferably a fluorinated fluorocarbon having a freezing point below that of the blood product and a boiling point above ambient temperature. The bottom surface of the container receives the heat transfer fluid both by rotating the container in a manner to be described and by the heat transfer fluid running down the exterior surface of the container. The fluid delivery system 40 includes a manifold inlet 62 which receives the inlet conduit 36. The manifold inlet 62 communicates with a cruciform-shaped junction 64 which divides the heat transfer fluid flow from the inlet conduit into three paths: a straight path 64a, and two paths 64b orthogonal to both the direction of inlet conduit fluid flow 36 and the manifold inlet 62. Each orthogonal outlet path 64b of the cruciform junction 64 communicates with two pairs of elbows 66 so that each elbow pair has an outlet on opposite sides of and running parallel to, but at a different elevation from a lower outlet that emanates from the cruciform junction 64 and defines the straight path.

All three outlets are in direct communication with linear perforated spray tubes 68. The tubes 68 are oriented so that the perforations triangulate at a central area with respect to the three spray tubes 68. The triangulation target at the central area is the container 80. All of the spray tubes reconnect to each other at an end of the spray tubes remote from the manifold inlet 62. The two spray tubes 68b which had communicated with elbows 66 at the inlet end, similarly have two more elbows 66 to return the tubing to the original elevation where it communicates with a T tube 72 and spray tube 68a which is closest to the door 14. All fluid passing through the inlet conduit 36 is delivered through the perforations in the spray tubes 68.

Figure 4:
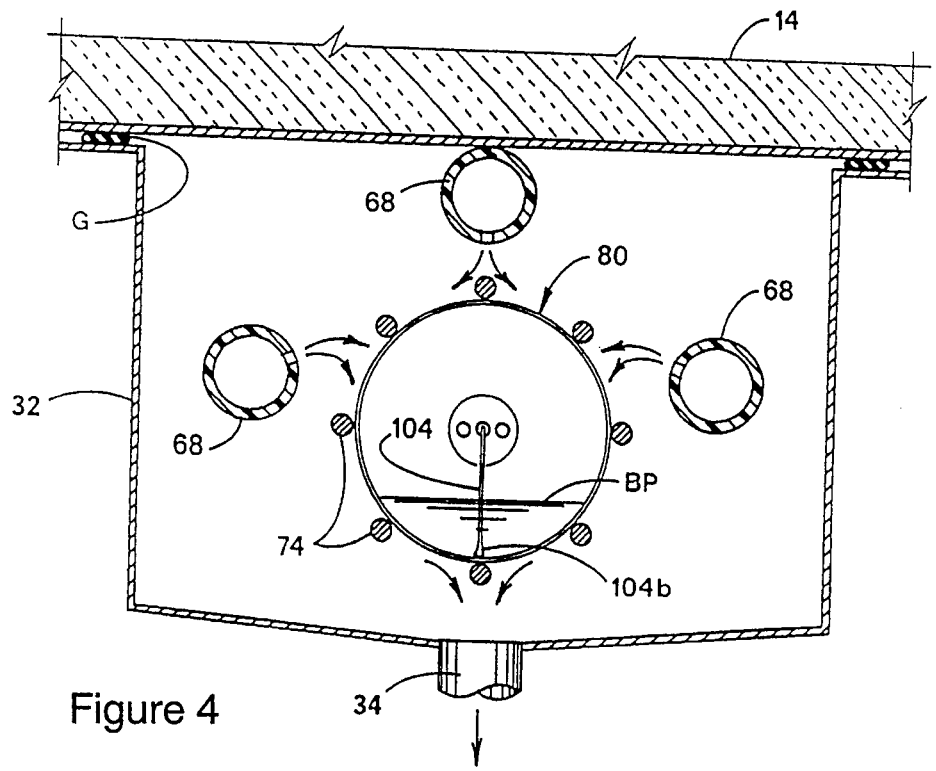
FIG. 4 illustrates one aspect of FIG. 3 in one phase.

FIG. 4 schematically depicts the manner in which the heat transfer fluid exits from the three spray tubes 68 and "triangulates" on the container 80. Note first that a gasket G circumscribes the well 32 and is carried on door 14 to preclude the through passage of any fluid mist beyond the well 32 and the door 14.

As shown in FIGS. 3 and 4, the container 80, 90 can be housed within a caged type receiver 20 which shall now be described. A plurality of spaced parallel elongate cage bars 74 are oriented in a cylindrical path and captured in fixed relationship by means of first and second spaced parallel substantially circular discs. Each disc is formed from two parts: a major segment 78 and a chord segment 76. The chord segment is adapted to move from a first closed position (as shown in FIG. 3 in solid lines) to a second open position (as shown in phantom in FIG. 3) to allow a container 80 to be placed therewithin. The chord segment pivots about one of the cage bars 74 along arrow "B" and secure the container 80 within the cage for subsequent manipulation. Closure of the cage 20 can be maintained by a hook H or a friction detent FD and protuberance PR. One longitudinal extremity of the cage receiver 20 includes a drive mechanism while another opposite longitudinal extremity includes an opening 82 within the disc chord segment 76 to provide a relief 82 for tubes communicating with the interior of the container 80 as will be explained.

Both disc major segments 78 include a spindle 84 which passes through a wall of the well 32. One spindle 84 is to be driven by means of a chain 88 operatively coupled to the spindle 84 by means of a sprocket 86. A second sprocket 86 is operatively connected to a motor 92 whereby rotation of the motor in either a clockwise or counter-clockwise direction will impart similar motion to the container via the cage through the chain and sprocket drive. The disc major segment 78 adjacent the relief 82 includes the second spindle 84 (not shown) similarly passing through the well 32 to support the cage receiver opposite end via a bearing race such as the one 85 shown in FIG. 3 on the motor end. The external diameter of the container is substantially that of the inner diameter of the cage 74 so that rotation of the cage frictionally induces rotation of the container.

FIG. 3 further reflects that the relief hole 82 formed in the chord segment 76 allows the through passage of tubes 94, 96 beyond the machine to communicate with the interior of the container. Essentially, the tube 94 defines an inlet tube through which the blood product passes. Tube 96 defines a vent tube 96 which allows communication with a source which either draws a vacuum or adds atmospheric pressure to the interior of the container 80. Because the container 80 and its associated cage 20 preferably rotate less than 360° and is in periodic, oscillatory motion, the tubes 94, 96 will not become kinked or fouled with other equipment.

The vent tube 96 is provided with the through passage of air by means of a pump 30, preferably a peristaltic type pump. As shown in FIG. 3, a cam surface of the pump 30 cooperates with a moveable jaw which can go from a first (phantom) to a second position that engages the vent tube 96 to provide cyclic and ongoing urging of air in one direction or the other through the vent tube 96.

An alternative to the cage and vacuum cooperation could take the form of retaining the container 80 by means of a series of circumscribing rollers 74b, 74c of FIG. 3A. Increased roller pressure on the container (via force F of a bellcrank type roller rod 75) would therefor "mimic" the implosion that occurs when the frozen blood product is subjected to the vacuum. At least one of the rollers e.g. 74c has means to move radially inward, shown as a gas shock 65 operating on a tail 73 of a pivoted roller rod 75.

As mentioned supra, maintaining an environment within the container 80 that is free from outside contamination is extremely desirable, if not essential. Two variations for maintaining the sterility within the container are shown in FIG. 3. In one form, the vent tube 96 communicates with a branch vent 96a and in turn with a bellows type bag 98 to assure that any air or gas migration is only properly sterile for optimum results. A second vent branch 96b reflects an alternative scenario where an appropriate filter 102 is in fluid communication with the interior of the container 80 through the pump 30 so that the sterile standards can be maintained without the need for a bellows bag. Presumably, should the apparatus 10 be situated within an operatory, the air therewithin shall be sterile as prescribed by standard medical procedure.

Figure 5:
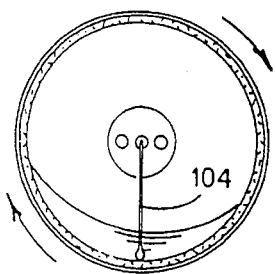
FIG. 5 illustrates another stage of the phase of FIGS. 3 and 4.
Figure 6:
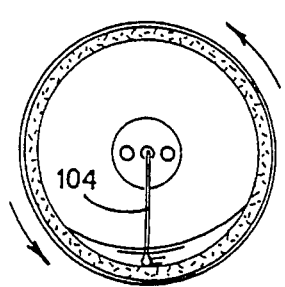
FIG. 6 shows a further stage.

Attention is now directed to FIGS. 4 through 10 which schematically depict one complete freezing and thawing cycle. Initially, the blood product BP is shown at rest as in FIG. 4 while cooling liquid is emitted from the spray tubes 68 from well 42 (FIG. 2). Preferably, rotation of the container is effected simultaneously with the spraying by rotation of the cage 20 within which the container 80 is housed. Cage rotation 20 is desired in both a counter-clockwise and clockwise direction in a periodic oscillatory manner. As the liquid blood product advances up on an interior wall of the container during rotation, a thin coating of the liquid is exposed to the cooling spray by thermal contact through the wall of the container 80. The remainder of the liquid tends to gravitate back to its lowermost energy level, near the bottommost portion of the container. However, the liquid's viscosity will cause a certain portion of the blood product to adhere to the sides of the container wall in response to container rotation. The rate at which the container is rotated coupled with the temperature differential associated with the refrigerant spray emanating from the outlets on the spray tubes 68 determine the rate at which a frozen "skin" will begin to form on an interior of the container 80. FIGS. 5 and 6 show a gradual increase in the thickness of the frozen blood product as rotation continues.

Figure 7:
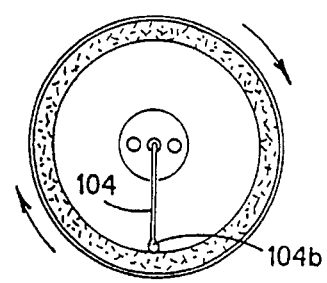
FIG. 7 shows a further stage.
Figure 8:
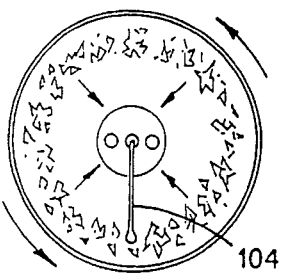
FIG. 8 shows a further stage.
Figure 9:
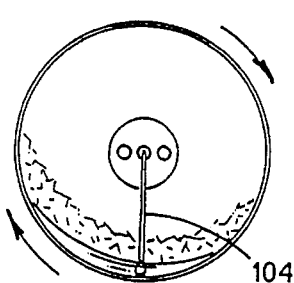
FIG. 9 shows a further stage.
Figure 10:
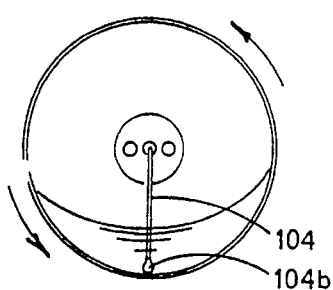
FIG. 10 shows a further stage.

Further liquid coats the interior of the container until FIG. 7 has been attained when all of the liquid will have been frozen. Preferably, at this instant, a spray of warm liquid from well 52 contacts the exterior surface of the container 80 while rotation continues. After a short interval of time, i.e. in the order of ten seconds, a vacuum is drawn on the interior of the container 80 by means of the pump 30. Because the blood product is frozen, and because the exterior walls of the container are sufficiently resilient to deform in the presence of a vacuum (especially after having been treated with the warm spray for a few seconds), the frozen blood product implodes within the container. The implosion results in a fine atomization of the frozen blood product (FIG. 8). Spraying of warm fluid continues carefully now so that the forming liquid within the container (FIG. 9) stays below 4° C. to prevent resolubilization of the fibrinogen back into the blood product. FIG. 10 shows the liquid at approximately 3° C. in suitable form for a second freezing as shown in the sequence beginning at FIGS. 4 and 5. Running the blood product through first and second freeze thaw cycles is believed to provide a relatively complete harvest of all available fibrinogen.

Note the presence of a temperature sensor 104 which is configured somewhat like a pendulum bob with the sensor head 104b located at the terminus of the pendulum. The temperature sensor 104 is configured to ride in the container at a lowermost area of the liquified blood product to provide an accurate indication of what the status of the liquid blood product is at the most important condition, i.e. nearest the phase change which occurs near the wall of the container. This always places the temperature sensor at the critical area of transition whether the change of phase is going from a liquid to a solid or from a solid to a liquid. The area of transition is intended to be within the liquid which is closest to the wall of the container.

It is possible that the temperature sensor may not be necessary in all situations especially if the change of phase times is substantially uniform for all donors. However, a temperature sensor may prove useful as a fail safe to assure that the fibrinogen does not resolubilize by having the liquid go above 4° C. It should be pointed out that the literature reports widely varying rates at which fibrinogen is harvested from blood products. This appears to derive from the lack of an efficient standard procedure for cryoprecipitation. If the volume of liquid to be used in the container is expected to be a constant it is suggested that the system may be automated for standardized cycles without the need for a temperature sensor.

Figure 11:
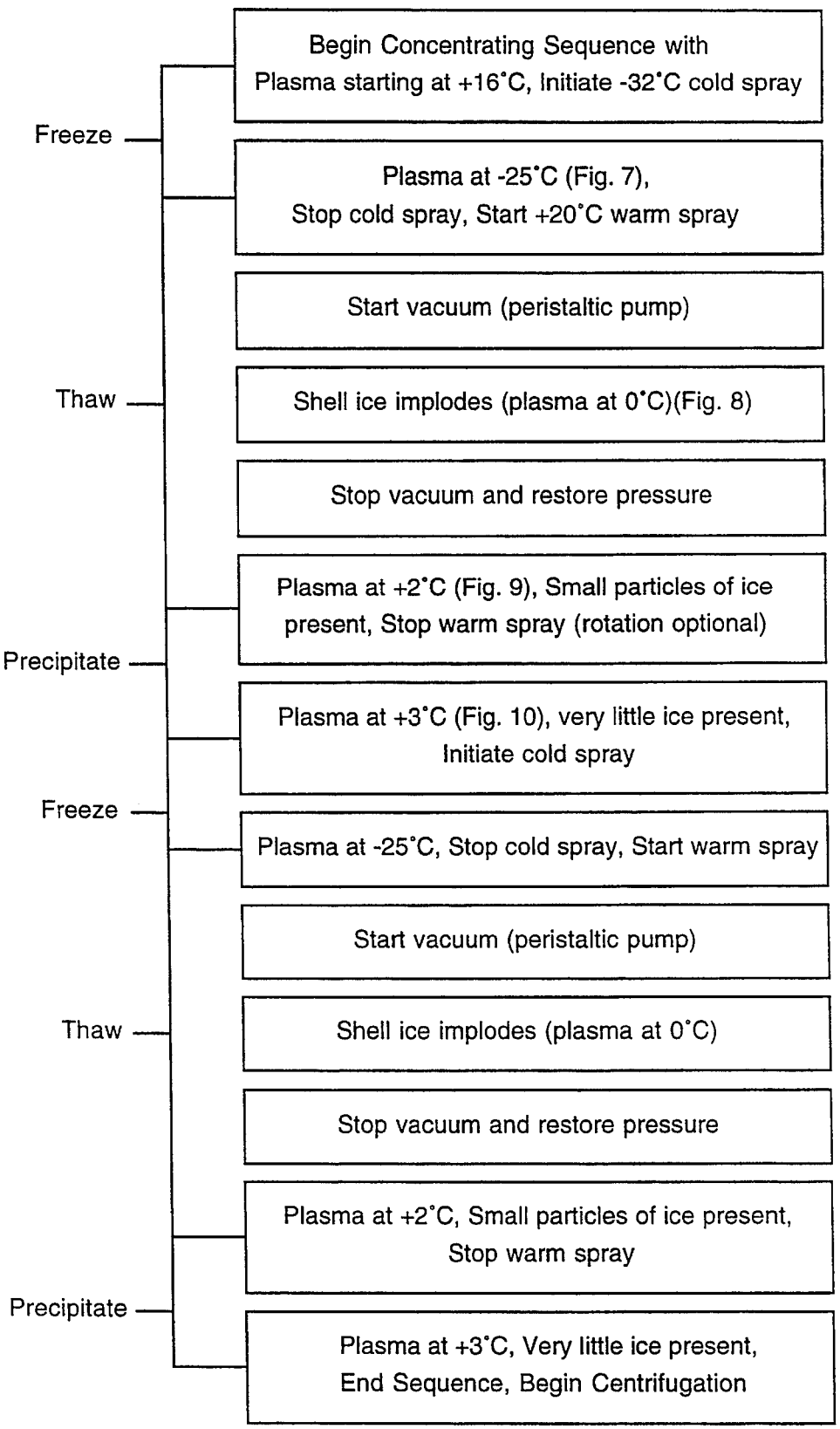
FIG. 11 is a flow chart of the stages reflected in FIGS. 4 through 10.
Figure 12:
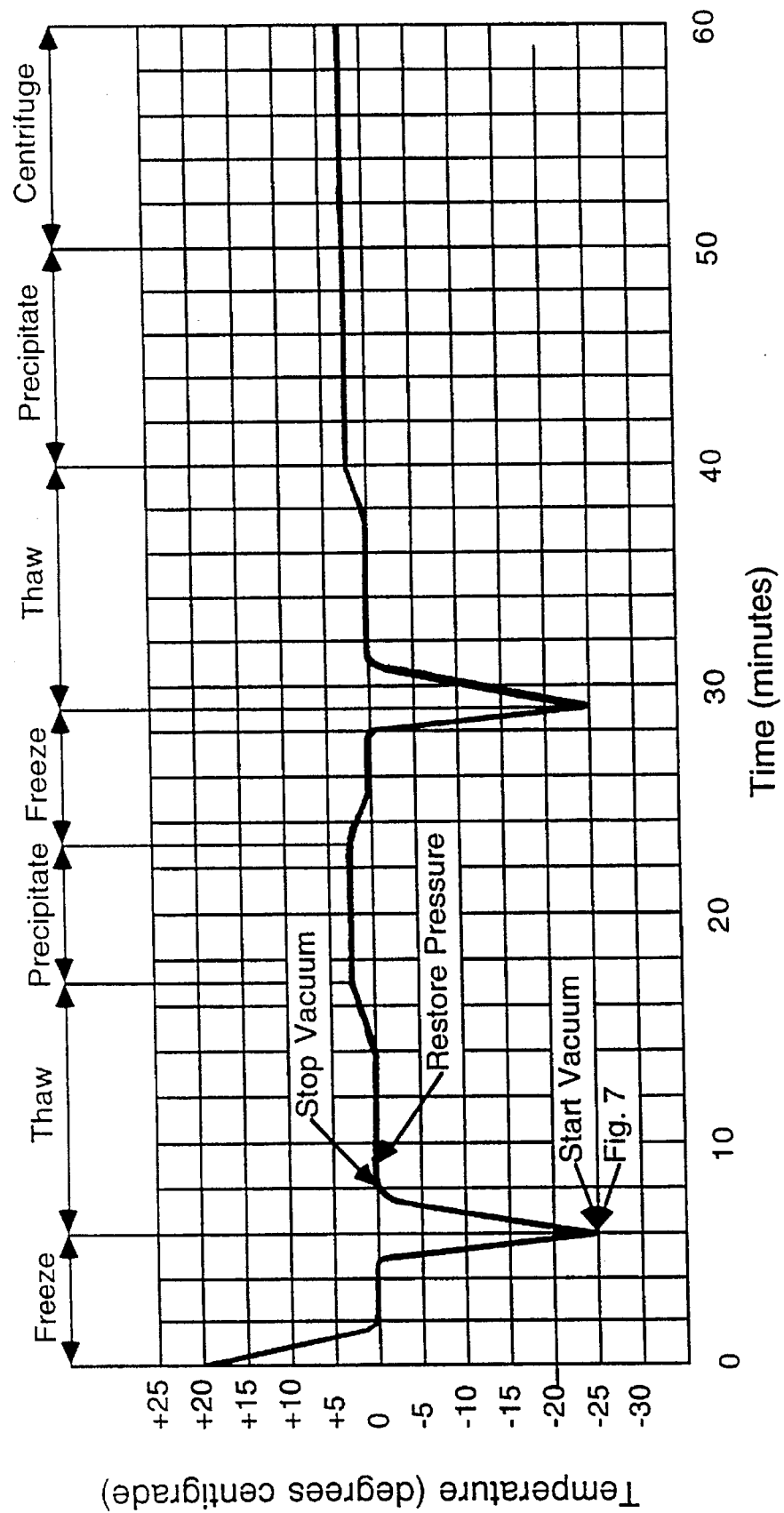
FIG. 12 is a graphic depiction associated with the steps of FIGS. 4 through 11.

FIGS. 11 and 12 reflect results developed to date by experimentation and include protocols for application of the vacuum and rotation of the container. As mentioned, the purpose for spraying the container with warm fluid for about ten seconds prior to application of the vacuum is to warm the container somewhat to restore or enhance its flexibility. Once the blood product implosion has occurred, the vacuum is released shortly thereafter and the expelled volume of air is returned to the container by the peristaltic pump operating in reverse.

Typically, and with reference to FIG. 12, the vacuum is started at about six minutes into the cycle and stopped about eight minutes into the cycle and pressure is restored at around nine minutes. Notice that the portion of the cycle from approximately seventeen minutes to twenty-three minutes (labeled "precipitate" at FIG. 12) may or may not be accompanied by rotation depending upon how best to optimize the precipitation of the protein within the container (at FIG. 9). This is also true for second (or any subsequent) precipitations in FIG. 12 when there are multiple freeze/thaw cycles.

Attention is now directed to FIGS. 13 through 15 which detail the container 80 mentioned hereinabove. In essence, the container 80 includes a cylindrical barrel 105 defining a central area, a tubing end 106 and a cryoprecipitate end 124. An area of transition exists between the cylindrical barrel 105 and the tubing end 106. As shown in FIG. 13, this transition takes the form of a linear, conical taper 122. Similarly, a transition is provided between the cryoprecipitate end 124 and the cylindrical barrel 105. As shown, the transition is in the form of a radiused taper 126.

The tubing end 106 includes a cap 116 on which an inlet coupling 108 is formed adapted to frictionally receive thereover the inlet tube 94. Similarly, a vent coupling 112 receives the vent tube 96 thereover. In addition, a temperature sensor coupling 114 is disposed between the inlet and vent couplings for operative communication with a control mechanism to dictate cycling of the apparatus 10 and its protocol. As shown, the temperature sensor coupling 114 appears substantially coaxial with the longitudinal axis of the container 80. The cap 116 further includes a radially extending annular flange 118 which is interposed between the couplings 108, 112, 114 and the conical taper 122. Preferably, flange 118 is integrally formed with the cap 116.

The cap 116 is fitted on to the container 80 in any suitable fashion.

The cryoprecipitate end 124 includes a cylindrical section 128 having a lesser radius than the cylindrical barrel 105 so that the radiused taper 126 converges towards the cryoprecipitate end 124. The cylindrical portion 128 includes a series of gradations 130 adjacent a visually transparent portion so that when the fibrinogen is visually differentiable from the non-precipitated fraction, the volume of fibrinogen can be noted. To this end, a label 132 is provided preferably on the cylindrical barrel 105 which can receive markings from a coating implement such as a pen to denote the reading derived from the gradations. This records the available volume of fibrinogen that has been cryoprecipitated. Later, when the cryoprecipitate has its temperature raised to facilitate removal from the cryoprecipitate end 124 it may not be visually discernable from the lighter unprecipitated fraction. It may be desirable to account for the cryoprecipitate as it is extracted to assure complete use.

A means for extraction of the cryoprecipitate is shown in FIG. 16. Essentially, a terminus of the cylindrical portion 128 includes a radially extending lip 134 against which a plug 136 abuts. The plug has a lower stopper 138 having a diameter substantially that of the outer periphery of the lip 134 and a necked down core 140 adapted to be received within the interior of the cylindrical portion 128. The necked down core 140 includes a plurality of radially extending ribs 142 having a plurality of notches 144 medially disposed along the height of the ribs so that the plug can be easily distorted for easy insertion with in the cylindrical portion 128. However, the ribs especially when coupled with the notches 144 act as cleats to resist removal of the plug 136. This is especially important because the container 80 is anticipated as being exposed to centrifugation and loading on the plug end.

In order to further retard the unwanted removal of the plug 136, a ferrule 146 is adapted to overlie both the stopper portion 138 of the plug 136 and engage the lip 134 of the cylindrical portion 128. The ferrule includes a shelf 148 adapted to overlie the lip 134 to retard egress. In addition, the ferrule 146 includes an access portal 162 on an end opposite shelf 148. The access portal 162 is dimensioned to receive a plate 158 frictionally therewithin and secured thereto. The plate 158 is part of a seal 156 which has an inner diameter complemental to the outer diameter of the ferrule to frictionally reside thereover and be retained thereagainst especially by the frictional contact that the plate enjoys in its overlying registry with the access portal 162. Thus, access to the plug 136 is not possible until the seal 156 has been removed. It is to be noted that the plate 158 is extremely difficult to reinsert through the access portal 162 because of the relative dimensions between the two and because of the resilient pressure exerted by the plug 136 against the interior of the ferrule 146 adjacent the access portal 162.

The plug 136 includes a dam 154 preferably formed from sealable material and placed in overlying registry with respect to the access portal 162 and therefore the plate 158. The dam 154 precludes access to the interior of the cylindrical portion 128 of the container 80 until penetration (e.g. as by a syringe) has been made, thereby gaining access to the interior of the cylindrical portion via a bore 152 which passes through the plug 136 along its axial center. The plug 136 is dimensioned such that the syringe will not extend deeply into the cylindrical portion. In fact it is desired that the syringe needle be retained within the bore 152. This increases the likelihood that the only fraction being extracted from the plug is the desired cryoprecipitate. In essence, as the cryoprecipitate is extracted by use of a syringe, the available cryoprecipitate is decremented on the label 132 to show the available amount so that fibrinogen usage will have been maximized.

Attention is now directed to FIGS. 17 through 20 which reflect alternatives to the container discussed with respect to FIGS. 13 through 15. It is to be noted that the cylindrical portion 128, plug 136, ferrule 146 and seal 156 could be used in the variations of FIGS. 17 through 20 and will not be belabored. In addition, the label 132 is intended to be used in this environment as well. Moreover, the inlet coupling 108 and vent coupling 112 are also intended for utilization in these variations.

In essence, FIGS. 17 through 20 reflect variations on plasma bags which are certainly adaptable for use in the instant invention. Generic plasma bags, however, have certain inefficiencies over which the bags disclosed in FIGS. 17 through 20 reflect improvements. For one thing, existing plasma bags do not readily lend themselves to centrifugation. Some fibrinogen could be lost or not harvested because of the existing plasma bag geometry. However, it will become evident that commercially existing plasma bags are also amenable to utilization with the instant device. The plasma bag shown in FIGS. 17 and 18 are substantially rectangular blanks formed from a first ply 164 which is welded to a second ply 166 along a peripheral border 168. The inlet and vent couplings 108 and 112 are disposed at a top portion of the bag 90a and spaced from one another by means of a support tab 172. A bottom of the bag 90a includes a taper where a bottom of the bag 90a converges towards the cylindrical portion 128 by means of converging edges 174. The cylindrical portion 128 is axially aligned with an opening 172a formed on the support tab 172.

FIG. 19 is similar to FIG. 17 with the exception that the bag is of pure rectangular shape and the support tab 172 and the cylindrical portion 128 are disposed upon a diagonal. The inlet coupling 108 and vent coupling 112 disposed on one side edge of the rectangle adjacent to the tab 172. Thus, both couplings are disposed on one side of the tab 172. By providing the cylindrical portion 128 at a corner and along a diagonal with respect to the tab 172, there is a natural funnelling action of the cryoprecipitate towards that end which achieves the same purpose that the converging end edges 174 of FIG. 17.

FIG. 20 is similar to FIG. 19 with the exception that the inlet coupling 108 and the vent coupling 112 straddle the tab 172. In view of the foregoing it should be clear that other geometrical rearrangements are now evident.

Figure 21:
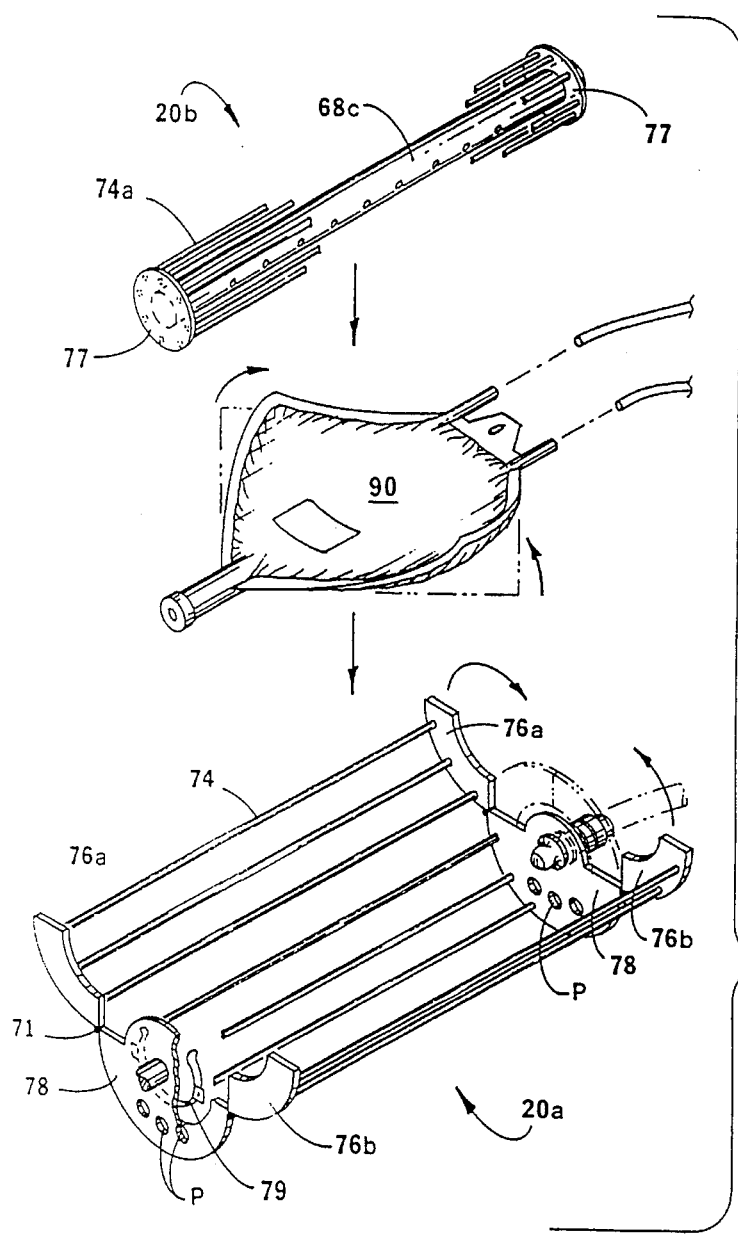
FIG. 21 is a perspective view of an alternative embodiment to that which is shown in FIGS. 3 and 4 when the alternative embodiment shown in FIGS. 17 through 20 are employed.

FIG. 21 reflects an alteration of the cage 20 which defines the receiver within which the container is to be disposed. In this version the chord segment 76 has been broken into two quadrants 76a and 76b. In addition, hinges 71 are shown connecting the chord segments to the major segment 78. As shown in FIG. 21, when the cage 20a is used, both chord segments are opened to form a cradle upon which the plasma bag 90 is placed. In addition, a cage core 20b may be included to lie atop the plasma bag 90 so that when the chord segments 76a and 76b are closed, the plasma bag 90 is constrained to form a substantially annular shape (FIG. 22) supported on an interior by the core cage 20b. In essence, the core cage 20b is formed from a plurality of cage bars 74a. Extremities of the cage bars 74a are supported by first and second annular discs 77. A spray bar 68c having a plurality of perforations therewithin allows heat transfer fluid to contact the inner annular surface of the plasma bag. The discs 77 are removeably attachable to the discs 78. As shown in FIG. 21, a spring biased clamp 79 is provided at one end of the disc 78 for frictional engagement about the outer periphery of the disc 77. At an opposite end, an inlet conduit 36a can communicate with the inner spray tube 68c by means of a connector 81 on disc 78. A check valve 83 yields and provides fluid access to an interior of the spray tube 68c by valve displacement through hollow pin 85 carried on disc 77 and which is circumscribed by a sleeve 87. Sleeve 87 rides over the coupling 81. This fluid feeds spray tube 68c. Discs 78 may be provided with a plurality of perforations P in order to facilitate drainage of the fluid caused by the core spray tube 68c. Alternatively, the bag shown as oriented in FIG. 22 could be inverted 180° so that the edges of the bag can face downwardly to provide natural fluid migration into the well.

Figure 22:
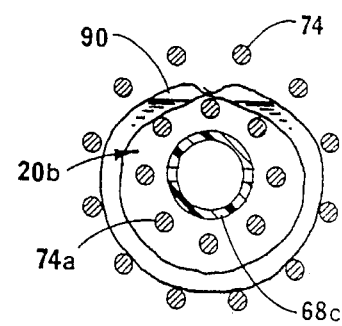
FIG. 22 is a transverse sectional view of that which is shown in FIG. 20 in one stage of assembly.
Figure 23:
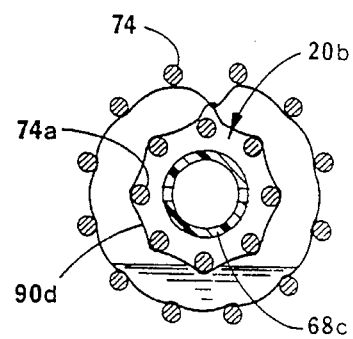
FIG. 23 is a second view of that which is shown in FIG. 22 at a second stage.
Figure 23A:
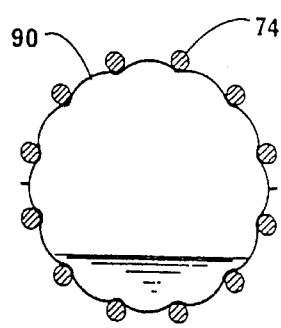
FIG. 23A is an alternative embodiment to that which is shown in FIG. 23.
Figure 24:
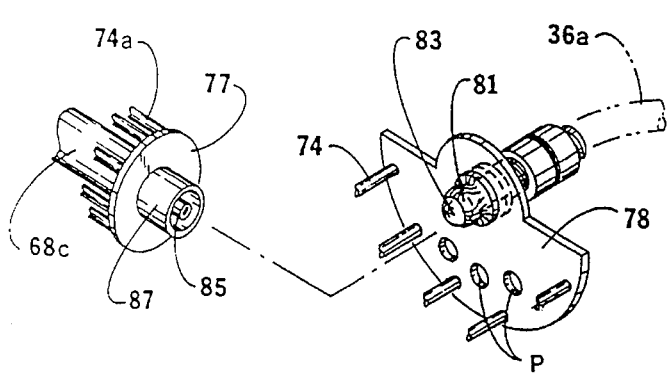
FIG. 24 is a detail of a portion shown in FIG. 21.

FIG. 22 reflects that the bag when so disposed within the FIG. 21 structure does not have a high degree of ullage or available air space. One of the attributes of the instant invention is to provide a thin coating on walls of a container such as the bag. It is possible to reverse the pump 30 to pressurize the plasma bag. This distends the bag 90 as shown in FIG. 23 by providing additional air so that the apparatus 10 discussed with respect to the container 80 is equally applicable here but with one notable difference. In addition to the exterior walls of the container having been coated with heat transfer fluid in the earlier examples, the present embodiment of FIG. 23 provides an additional surface area for coating. The inner annular surface 90d is formed by having circumscribed the core 20b discussed with respect to FIG. 21. Thus, an appreciable increase in surface area will have been manifested by using a bag type container. FIG. 23A shows a similar, distended bag without the core 20b.

FIGS. 25 through 28 reflect various permutations and combinations that have been mentioned briefly with respect to the pump 30, container 80 and use of a bellows bag 98 or filter 102. Various permutations should now be evident.

Figure 29:
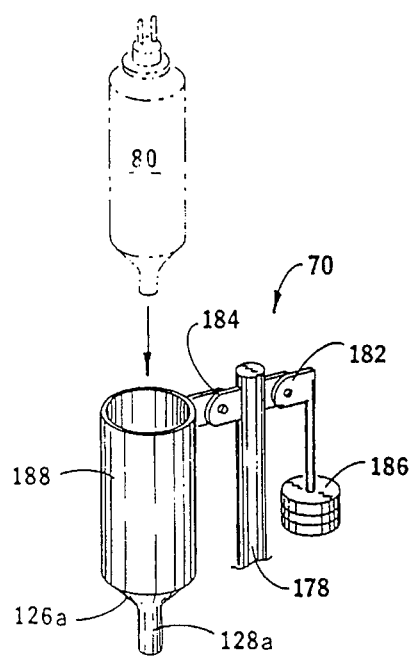
FIG. 29 is a perspective view of the centrifuge apparatus according to the present invention.
Figure 30:
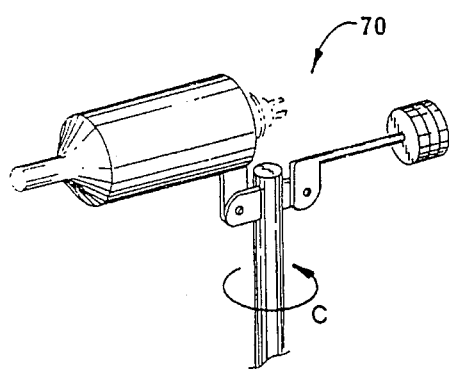
FIG. 30 depicts FIG. 29 with centrifugation in effect.
Figure 31:
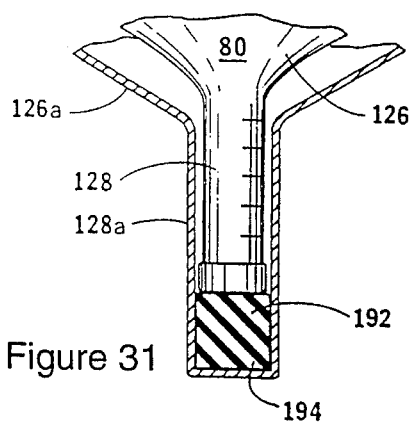
FIG. 31 shows a detail of the bottom portion of FIG. 29 in an unstressed state.
Figure 32:
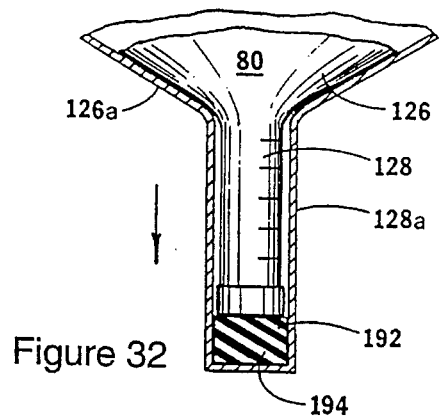
FIG. 32 shows a view similar to FIG. 31 in a stressed state.

Attention is now directed to FIGS. 29 through 33 which show details of the centrifuge 70 contained within the box 22 of FIG. 1. Specifically, FIGS. 29 and 30 shows a centrifuge contoured for the container 80. A shaft 178 is adapted to rotate along the direction of the arrow "C" in response to excitation from a motor (not shown). The shaft is coupled to a counter balance weight 186 at one extremity of an interposed connecting ear 182. Another connecting ear 184 couples the shaft 178 to a sleeve 188 having a contour substantially complemental to the container 80. Thus, the sleeve 188 includes a substantially cylindrical section which complements the outer contour of the container 80 and includes a taper 126a adapted to support the radiused taper 126 of the container 80. In addition, a cylindrical portion 128a is provided which slideably receives therein the cylindrical portion 128 of the container 80. This detail is shown in FIGS. 31 and 32.

A damper 192 is provided in a blind bore 194 included with the cylindrical portion 128a. The damper 192 is fixed at a lowermost portion of the blind bore 194 and is adapted to compress as shown in FIG. 32 in response to centrifugation which causes centrifugal forces to be exerted at the blind bore 194 as a result of rotation about the shaft 178 in the direction of the arrow "C" shown in FIG. 30. By compressing the damper 192, it is assured that load distribution is shared by the radiused taper 126 as it abuts against the taper 126a other centrifuge's sleeve. Note that the damper in FIG. 32 reflects compression which assures tangential registry of the radiused taper 126 against the taper 126a of the sleeve.

Figure 33:
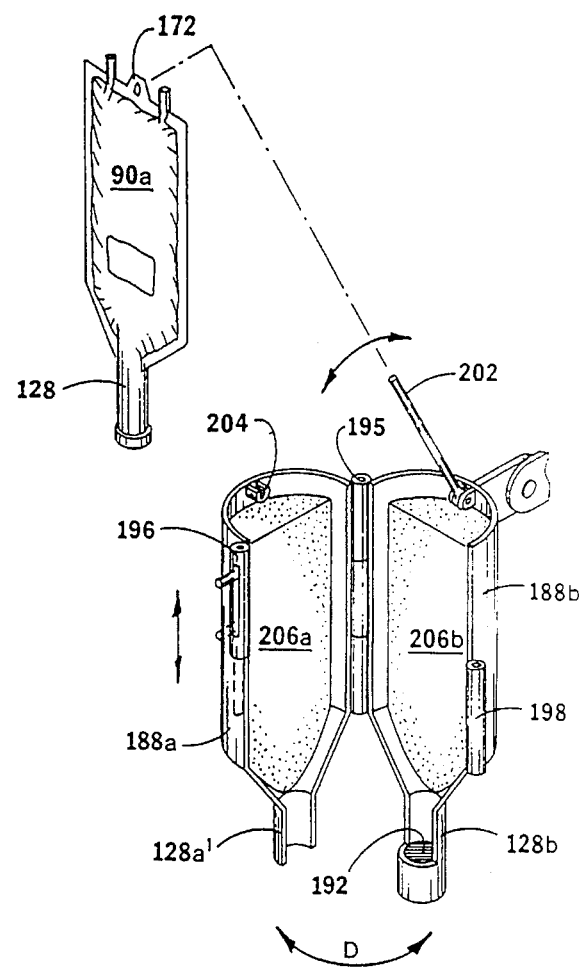
FIG. 33 shows an alternative centrifuge receiver compared to that which is shown in FIG. 29.

Another centrifuge is shown in FIG. 33 to accommodate the plasma bags 90, of which bag 90a is illustrated. In this event, the sleeve 188 is formed from a shell having two components 188a and 188b adapted to move from an open to a closed position as shown by the arrow "D" about a hinge 195. A sliding bolt 196 cooperates with a bolt receiver 198 to lock the sleeve halves 188a, 188b together. The tab 172 of the bag 90a is supported upon a rod 202 which is pivoted on one-half of the sleeve 188b and has a shoulder support 204 on a diametrically opposed corresponding location on the other half of the sleeve 188a. In addition, a pair of liner constraints 206a and 206b reside within the sleeve halves 188a and 188b respectively, so that the contour of the bag remains somewhat preserved while the cylindrical portion 128 is slideably received within a corresponding portion at a lowermost end of the sleeves 188a and 188b. Thus, a semi-cylindrical section 128a' communicates with another portion 128b to seal the cylindrical portion 128 above the plug 192 which is captured within a non-separable blind bore. The liner constraints 206a and 206b can be contoured complemental to the other bags shown in FIGS. 19 and 20 as should now be evident.

Figure 34:
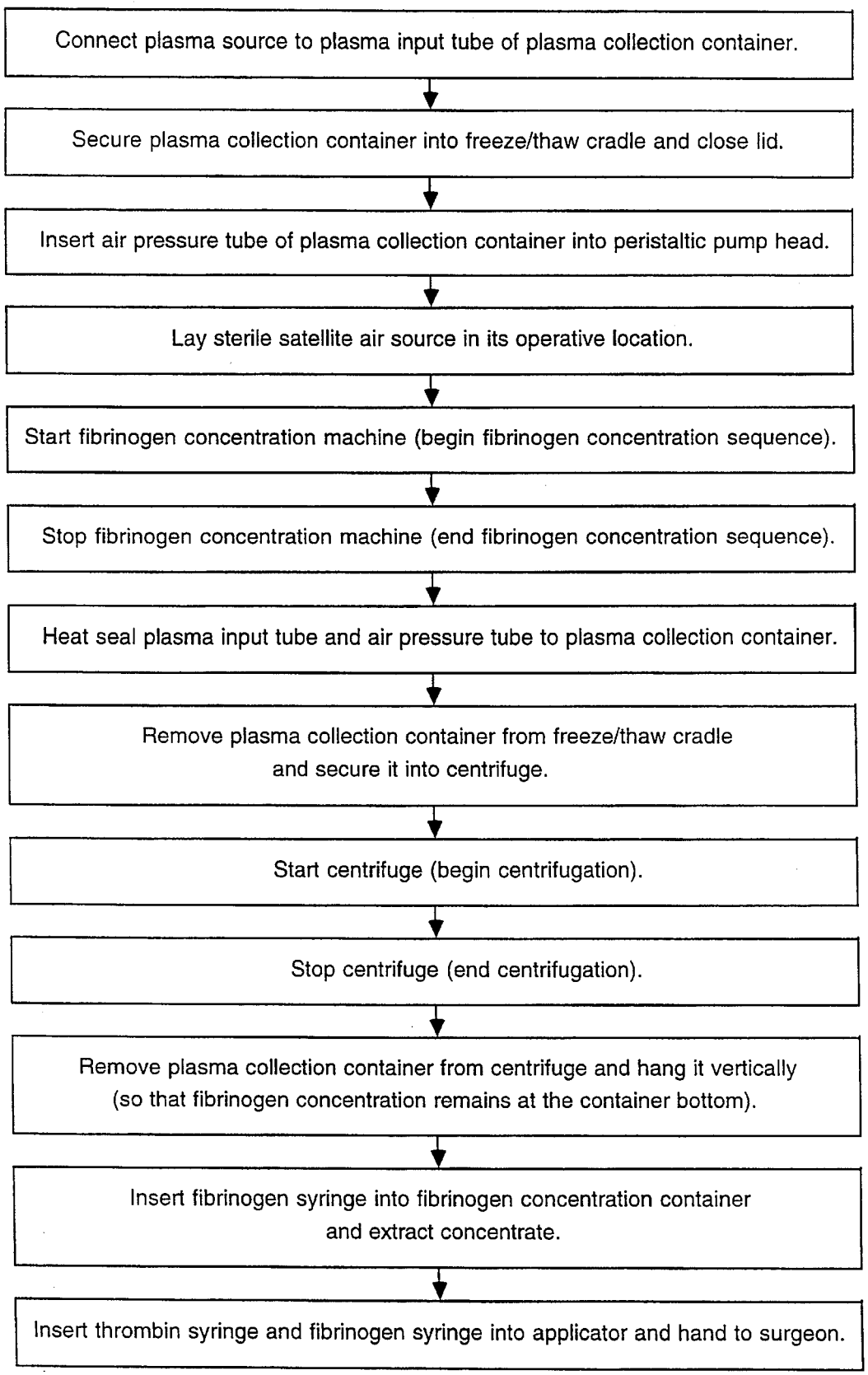
FIG. 34 is a flow chart showing the overall sequence of steps inclusive of the FIG. 11 detailed methodology.

FIG. 34 substantially recaps the foregoing description of the preferred embodiment and describes utilization of the apparatus by way of example. Two further components of FIG. 1 can be described in light of the foregoing. As shown in FIG. 1, a wand 212 is provided which is coupled to a source of power through a cable 214 to provide heating. The wand 212 has a closeable jaw 216 at one end opposite a handle area. The jaws 216 are intended for use with the inlet tube 94 and vent tube 96. As mentioned above, it is essential that a sterile environment be maintained to the extent possible. Once the blood product has been introduced into the container 80 or bag 90, it may be desirable to seal off the inlet tube 94 by means of heat sealing. The jaws 216 of the wand 212 will heat seal the tube. In addition, the vent tube 96 should be sealed particularly prior to centrifugation. The jaws 216 of the wand 212 can also perform this function. The wand 212 is intended to reside on a dowel 218 carried on a side wall 4 of the lower carton 2. In addition, the wand 212 may have an annular heating element 222 having an internal dimension adapted to circumscribe the cylindrical portion 128 of the cryoprecipitate end of either the container 80 or the bag 90. The annular heating element 222 when placed around the cylindrical portion 128 can be controlled to heat the fibrinogen that has been cryoprecipitated after centrifuging so that it can be easily drawn from that cylindrical portion 128 through a syringe as described hereinabove.

One side wall 4 of the carton 2 includes a holder 232 for bag 90 or container 80. The flange 118 of container 80 rests atop the two prongs defining the holder 232. For bag 90, tab hole 172a receives one prong. In each case, the bag 90 or container 80 is properly oriented for extraction of the fibrinogen with a syringe from this holder after centrifuging.

The top surface 12 of the carton 2 of FIG. 1 also includes an on/off switch S and a timer T coupled with indicator lights I intended to show the status of the cryoprecipitation. The timer T may control the rate at which the motor 60 rotates and switch S could be used to initiate the cycle. The upper box 22 also includes a switch S for initiating the centrifugation operation along with an indicator light I for indicating the status of the centrifuge. FIG. 2 shows the cooperation of a controller with the peristaltic pump 30, rotating motor 60, valves V1, V2 and fluid pumps 48, 58. The fluid in both wells 42 and 52 is preferably fluorinated fluorocarbons. Thus, the fluids in the wells can intermingle without disadvantage. Moreover, fluorinated fluorocarbon has a high vapor pressure, evaporates with no residue, is non-toxic and non-flammable. Fluorinated fluorocarbon also has a freezing point substantially lower than the freezing point (e.g. lower than −30° C.) of the liquid inside the container and has a boiling point significantly higher than normal ambient temperatures (e.g. greater than +30° C.).

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. An apparatus for extracting fibrinogen from a blood product, comprising in combination:

a closed container having an interior and an exterior, said interior isolated from said exterior, vent means coupled to said closed container to allow said interior to change pressure, the blood product at one temperature and disposed within said interior of said container, said container having an interior volume including ullage within said container so that the container is only partially filled with the blood product and the remainder of the container holds gas to allow the blood product to form a film on said interior of said container, a container support for removably receiving and retaining said container to a housing of said apparatus, said container support orienting said vent means above the blood product in said ullage, means to move said container via said support so that the film of the blood products coats said interior of said container free from said vent means, and temperature means for freezing and thawing the film of the blood product, said temperature means juxtaposed proximate said exterior of said container to alter a temperature profile of the blood product by thermal exchange through said container and through the film as it coats said interior of said container while said container moving means operates.

2. The apparatus of claim 1 wherein said means to move said container includes a means to rotate said container, whereby said thin film is deposited upon said interior of said container.

3. An apparatus for extracting fibrinogen from a blood product, comprising in combination:

a container, blood product at one temperature disposed within said container, said container having sufficient volume to include ullage within said container so that said container is only partially filled with the blood product and the blood product is capable of forming a film on an interior of said container, a container support, means to move said container so that a film of the blood products coats an interior of said container, and temperature means for creating a phase change between a liquid phase and a solid phase in the film of the blood product; and vice versa, said temperature means juxtaposed proximate an exterior of said container and integrally formed with said apparatus to alter a temperature profile of the blood product by thermal exchange through said container and through the film as it coats said container during container motion, said container support removably securing said container adjacent to said temperature means for creating the phase change of said film, and wherein said apparatus includes pressure differential means in communication with an interior of said container to provide a pressure gradient in said container when compared to ambient conditions, said means to move said container operating concurrently with said temperature means.

4. The apparatus of claim 3 wherein said pressure differential means includes a source for receiving and providing sterile gas, said source of sterile gas in communication with said interior of said container through said pressure differential means, such that when gas is removed to provide the pressure gradient, said source of sterile gas receives said removed gas, and when gas is added to provide the pressure gradient, said source of sterile gas delivers said added gas.

5. The apparatus of claim 3 wherein said temperature means for creating the phase change includes a first heat transfer fluid stored in a reservoir and including means for maintaining a temperature differential with the heat transfer fluid and the blood product.

6. The apparatus of claim 5 wherein said first heat transfer fluid is fluorinated fluorocarbon wherein the fluorinated fluorocarbon causes the blood product to be cooled and heated thereby, causing phase change of the blood product.

7. The apparatus of claim 3 wherein said pressure differential means includes a pump in fluid communication with said ullage of said container, whereby a pressure within said container is adjustable.

8. An apparatus for extracting fibrinogen from a blood product, comprising in combination:

a closed container having a vent, blood product at one temperature disposed within said container, said container having sufficient volume to include ullage within said container so that the container is only partially filled with the blood product and the blood product is capable of forming a film on a interior of said container, a container support, means to move said container so that a film of the blood product coats said interior of said container while said vent is exposed to the ullage, and temperature means for creating a phase change between a liquid phase and a solid phase in the film of the blood product; and vice versa, said temperature means juxtaposed proximate said exterior of said container and integrally formed with said apparatus to alter a temperature profile of the blood product by thermal exchange through said container and thorough the film as it coats said container during container motion, said container support removably securing said container adjacent to said temperature means for creating the phase change of said film, wherein said means to move said container includes a means to rotate said container, whereby said thin film is deposited upon said interior of said container, and wherein said means to rotate said container includes means for periodically and repetitively moving said container through an arc of a circle, said means to move said container operating concurrently with said temperature means.

9. An apparatus for extracting fibrinogen from a blood product, comprising in combination:

a container having vent means, blood product at one temperature disposed within said container, said container having sufficient volume to include ullage within said container so that said container is only partially filled with the blood product and the blood product forms a film on an interior of said container, said interior isolated from an exterior of said container, a container support, means to move said container so that a film of the blood products coats said interior of said container, and temperature means for creating a phase change between a liquid phase and a solid phase in the film of the blood product; and vice versa, said temperature means juxtaposed proximate said exterior of said container and integrally formed with said apparatus to alter a temperature profile of the blood product by thermal exchange through said container and through the film as it coats said container during container motion, said container support removably securing said container adjacent to said temperature means for creating the phase change of said film, wherein said means to move said container includes a means to oscillate said container in a periodic manner through an arc of a circle, whereby said film is deposited upon said interior of said container, and said means to move said container operating concurrently with said temperature means.

10. An apparatus for extracting fibrinogen from a blood product, comprising in combination:

a container, blood product at one temperature disposed within said container, said container having sufficient volume to include ullage within said container so that said container is only partially filled with the blood product and the blood product is capable of forming a film on an interior of said container, a container support, oscillatory means to move said container so that a film of the blood product coats said interior of said container by periodic rocking, and temperature means for creating a phase change between a liquid phase and a solid phase in the film of the blood product; and vice versa, said temperature means juxtaposed proximate said exterior of said container and integrally formed with said apparatus to alter a temperature profile of the blood product by thermal exchange through said container and through the film as it coats said container during container motion, said container support removably securing said container adjacent to said temperature means for creating the phase change of said film, and wherein said temperature means for creating a phase change includes a heat transfer fluid, said apparatus including a means to contact said heat transfer fluid against said exterior of said container, whereby heat transfer is stimulated through said container, said means to move said container operating concurrently with said temperature means.

11. An apparatus for extracting fibrinogen from a blood product, comprising in combination:

a closed container having vent means, blood product at one temperature disposed within said container, said container having sufficient volume to include ullage defined by blood product and gas within said container so that said container is only partially filled with the blood product and gas fills said container so that the blood product is capable of forming a film on an interior of said container, a container support, oscillating means to repetitively move said container through an arc so that a film of the blood product coats said interior of said container, and temperature means for creating a phase change between a liquid phase and a solid phase in the film of the blood product; and vice versa, said temperature means juxtaposed proximate said exterior of said container and integrally formed with said apparatus to alter a temperature profile of the blood product by thermal exchange through said container and through the film as it coats said container during container motion, said container support removably securing said container adjacent to said temperature means for creating the phase change of said film, and said means to move said container operating concurrently with said temperature means.

12. An apparatus for extracting fibrinogen from a blood product, comprising in combination:

a sealed container, blood product at one temperature disposed within said container, said container having sufficient volume to include ullage within said container so that said container is only partially filled with blood product and the blood product is capable of forming a film on an interior of said container, said interior isolated from an exterior of said container, a container support, means to move said container so that a film of the blood product coats said interior of said container, and temperature means for creating a phase change between a liquid phase and a solid phase in the film of the blood product; and vice versa, said temperature means juxtaposed proximate said exterior of said container and integrally formed with said apparatus to alter a temperature profile of the blood product by thermal exchange through said container and through the film as it coats said container during container motion, said container support removably securing said container adjacent to said temperature means for creating the phase change of said film, and wherein said apparatus includes a means to increase a surface area of the blood product within said container when at least a portion of the blood product is in a solid phase, said means to move said container operating concurrently with said temperature means.

13. An apparatus for extracting fibrinogen from a blood product, comprising in combination:

a container, blood product at one temperature disposed within said container, said container having sufficient volume to include ullage within said container so that the container is only partially filled with the blood product and the blood product is capable of forming a film on the interior of said container, a container support, means to move said container so that a film of the blood product coats an interior of said container, and temperature means for creating a phase change between a liquid phase and a solid phase in the film of the blood product; and vice versa, said temperature means juxtaposed proximate an exterior of said container and integrally formed with said apparatus to alter a temperature profile of the blood product by thermal exchange through said container and through the film as it coats said container during container motion, said container support removably securing said container adjacent to said temperature means for creating the phase change of said film, and wherein said apparatus includes a means to increase a surface area of the blood product within said container when at least a portion of the blood product is in a solid phase, said means to move the container operating concurrently with said temperature means, wherein said surface area increasing means includes a means to fragment portions of the blood product in a solid phase into a greater number of individual solid pieces, whereby the surface area of the blood product is increased.

14. A device for precipitation of fibrinogen from blood products comprising in combination:

a closed container with walls enclosing blood products within an interior thereof, a vent passing through said container, said container having a volume greater than a volume of the blood products therein to provide a gas in said container, a means oriented outside of said container to induce a phase change of said blood products first between a liquid phase and a solid phase, and back to a liquid phase, and an oscillating means for creating a film of the blood products upon said walls of said container, said film creating means including a means to concurrently operate with said phase change inducing means.

15. The device of claim 14 including said container having ullage defined by an enclosed volume greater than a volume of blood product disposed therein.

16. The device of claim 14 wherein said phase change inducing means is a heat transfer fluid juxtaposed adjacent an exterior of said walls of said container, said heat transfer fluid having a temperature distinct from a temperature of the blood products.

17. The device of claim 16 wherein said film creating means includes a means to completely rotate said container.

18. A device for precipitation of fibrinogen from blood products comprising in combination:

a sealed container with walls enclosing blood products within an interior thereof, means oriented outside of said container to induce a phase change of said blood products between a liquid phase and a solid phase, and vice versa, and a means for creating a film of the blood products upon said walls of said container, said film creating means including means to concurrently operate with said phase change inducing means, wherein said device includes said container having ullage defined by said container having an enclosed volume greater than a volume of blood product disposed therein, wherein said phase change inducing means is a heat transfer means juxtaposed adjacent an exterior of said walls of said container, said heat transfer means having a temperature distinct from a temperature of the blood products, wherein said film creating means includes a means to repeatedly oscillate said container through an arc.

19. The device of claim 18 wherein said device includes means to retain said container while allowing said heat transfer means embodied in the form of fluid to be sprayed out of spraying means to impact said container, said retaining means operatively coupled to said means to oscillate said container, including a motor with a rotatable output shaft, a first sprocket attached to said output shaft, a second sprocket attached to said retaining means and a chain interposed between said sprockets, whereby when said output shaft of said motor rotates, said chain causes said container coupled to said retaining means to rotate.

20. The device of claim 19 including a roller adjacent an exterior of said container, said roller operatively coupled to a rotational input means, wherein said rotational input means causes said roller to rotate, causing said container adjacent thereto to rotate.

21. A device for precipitation of fibrinogen from blood products comprising in combination:

a container with walls enclosing blood products therein, a means oriented outside of said container to induce a phase change of said blood products between a liquid phase and a solid phase and vice versa, and a means for creating a film of the blood products upon said walls of said container, said film creating means including means to concurrently operate with said phase change inducing means, wherein said device includes said container having ullage defined by said container having an enclosed volume greater than a volume of blood product disposed therein, wherein said phase change including means is a heat transfer fluid juxtaposed adjacent an exterior of said walls of said container, said heat transfer fluid having a temperature distinct from a temperature of the blood products, wherein said film creating means includes a means to rotate said container, and wherein said heat transfer fluid is juxtaposed adjacent an exterior of said walls of said container through a spraying means, said spraying means directing said heat transfer fluid against said exterior of said walls of said container, whereby a residence time of portions of said heat transfer fluid adjacent said container is reduced and a temperature increase of said portions of said heat transfer fluid adjacent said container is reduced, and wherein a means to draw a vacuum is operatively coupled to an interior of said container.

22. A device for precipitation of fibrinogen from blood products comprising in combination:

a container with walls enclosing blood products therein, a means oriented outside of said container to induce a phase change of said blood products between a liquid phase and a solid phase and vice versa, and a means for creating a film of the blood products upon said walls of said container, said film creating means including means to concurrently operate with said phase change including means, wherein said device includes said container having ullage defined by said container having an enclosed volume greater than a volume of blood product disposed therein, wherein said phase change inducing means is a heat transfer fluid juxtaposed adjacent an exterior of said walls of said container, said heat transfer fluid having a temperature distinct from a temperature of the blood products, wherein said film creating means includes a means to rotate said container, and wherein said heat transfer fluid is juxtaposed adjacent an exterior of said walls of said container through a spraying means, said spraying means directing said heat transfer fluid against said exterior of said walls of said container, whereby a residence time of portions of said heat transfer fluid adjacent said container is reduced and a temperature increase of said portions of said heat transfer fluid adjacent said container is reduced, and wherein said device includes a means to increase a surface area of the blood products within said container when said blood products are in a solid phase.

23. The device of claim 22 wherein said surface area increasing means includes a means to shatter said solid blood products into a greater number of individual solid pieces.

24. A device for precipitation of fibrinogen from blood products comprising in combination:

a container with walls enclosing blood products therein, a means oriented outside of said container to induce a phase change of said blood products between a liquid phase and a solid phase and vice versa, and a means for creating a film of the blood products upon said walls of said container, said film creating means including means to concurrently operate with said phase change inducing means, wherein said device includes said container having ullage defined by said container having an enclosed volume greater than a volume of blood product disposed therein, wherein said phase change inducing means is a heat transfer fluid juxtaposed adjacent an exterior of said walls of said container, said heat transfer fluid having a temperature distinct from a temperature of the blood products, wherein said film creating means includes a means to rotate said container, and wherein said heat transfer fluid is juxtaposed adjacent an exterior of said walls of said container through a spraying means, said spraying means directing said heat transfer fluid against said exterior of said walls of said container, whereby a residence time of portions of said heat transfer adjacent said container is reduced and a temperature increase of said portions of said heat transfer fluid adjacent said container is reduced, and wherein said device includes a first reservoir containing said heat transfer fluid including means to heat said heat transfer fluid to a temperature above a temperature of the blood products and a second reservoir containing said heat transfer fluid including means to cool said heat transfer fluid to a temperature below a temperature of the blood products, said spraying means selectively coupleable to both said first reservoir and said second reservoir along a pathway.

25. A device for precipitation of fibrinogen out of blood products comprising in combination:

a closed enclosure having a wall isolating an interior of said enclosure containing blood products therein from an exterior of said enclosure, venting means passing through said wall, said enclosure having a greater volume than a volume of blood products within said enclosure so that gas is within said enclosure, said enclosure volume sufficient to receive blood product from one donor for autologous production of fibrinogen, means to cause periodic motion between the container and the blood products to form a film build up of the blood products on an interior surface of said wall, and means to change a phase of the film of blood products between a liquid phase and a solid phase, and then back to liquid, concurrently with said means to cause periodic motion.

26. The device of claim 25 wherein said film forming means includes a means to rotate said enclosure about an axis of rotation such that portions of the blood products which are in a liquid phase are caused to migrate downward and form said film upon said interior surface of said wall.

27. The device of claim 26 wherein said phase changing means is a heat transfer fluid juxtaposed adjacent an exterior of said enclosure, said heat transfer fluid having a temperature distinct from a temperature of the blood products.

28. A device for precipitation of fibrinogen out of blood products comprising in combination:

an enclosure having a wall isolating an interior of said enclosure containing blood products therein from an exterior of said enclosure, means to cause relative motion between the container and the blood products to form a film of the blood products on said wall, and means to change a phase of the film of blood products between a liquid phase and a solid phase; and vice versa concurrently with said means to cause relative motion, wherein said film forming means includes a means to rotate said enclosure about an axis of rotation such that portions of the blood products which are in a liquid phase are caused to migrate downward and form said film upon said interior surface of said wall, wherein said phase changing means is a heat transfer fluid juxtaposed adjacent an exterior of said enclosure, said heat transfer fluid having a temperature distinct form a temperature of the blood products, and wherein said device includes a means to shatter said film of blood products when said film of blood products is in a solid phase, whereby a surface area of the blood products in said enclosure is increased.

29. The device of claim 28 wherein said shattering means includes a means to create a vacuum within said interior sufficient to cause said film of blood products to implode away from said wall of said enclosure.

30. The device of claim 28 wherein said heat transfer fluid includes a first temperature heat transfer fluid maintained at a temperature greater than a temperature of the blood products and a second temperature heat transfer fluid maintained at a temperature lower than a temperature of the blood products.

31. The device of claim 30 wherein said device includes a first reservoir housing said first temperature heat transfer fluid, said first reservoir including a means to heat said first heat transfer fluid and a second reservoir housing said second heat transfer fluid, said second reservoir including means to cool said second heat transfer fluid, said first reservoir and said second reservoir coupled to a pathway extending from said first reservoir and said second reservoir to an exterior of said enclosure.

32. The device of claim 31 wherein said device includes a means for spraying one of said heat transfer fluids adjacent an exterior of said enclosure, said spraying means including means to be in fluid communication with both said first reservoir and said second reservoir, said spraying means keeping said heat transfer fluid moving such that a temperature differential between said heat transfer fluid and blood products is maximized.

33. An apparatus for extracting fibrinogen from a blood product, comprising in combination:

a closed container having a blood product disposed within an interior of said container, said container having a greater free available volume than a volume of blood product within said container so that gas resides therewithin, venting means in said container, means to move said container relative to the blood product so that a film of the blood product coats said interior of the container, and means for creating a phase change between a liquid phase and a solid phase, and vice versa, in the blood product, said phase change means disposed outside of said container and including means to operate concurrently with said moving means, whereby the blood products change phase and fibrinogen precipitates therefrom as a result of said phase change.

34. A apparatus for extracting fibrinogen from a blood product, comprising in combination:

a container having a blood product disposed within said container, said container having a greater volume than a volume of blood product within said container, means to move said container relative to the blood product so that a film of the blood product coats an interior of the container, and means for creating a phase change between a liquid phase and a solid phase, and vice versa, in the blood product, said phase change means disposed outside of said container and including means to operate concurrently with said moving means, whereby the blood products change phase and fibrinogen precipitates therefrom as a result of said phase change, and wherein said phase change creating means includes a means to change a pressure within said container, said pressure changing means including a means to apply a compressive force to said container.

35. The apparatus of claim 34 wherein said pressure changing means includes a pump in fluid communication with an interior of said container.

36. The apparatus of claim 34 wherein said phase change means includes a means to change a temperature of the blood product.

37. The apparatus of claim 36 wherein said temperature change means includes a heat transfer fluid having a temperature distinct from a temperature of the blood product, said heat transfer fluid juxtaposed adjacent an exterior of said container such that heat transfer occurs between said heat transfer fluid and the blood product until a phase change occurs in the blood product.

38. An apparatus for extracting fibrinogen from a blood product, comprising in combination:

a container having a blood product disposed within said container which has sufficient volume to include ullage within said container so that said container is only partially filled with the blood product and the blood product is capable of forming a film on an interior of said container, means to move said container relative to the blood product so that a film of the blood product coats said interior of the container, and means for creating a phase change between a liquid phase and a solid phase in the blood product, said phase change means disposed outside of said container and including means to operate concurrently with said moving means, whereby the blood products change phase and fibrinogen precipitates therefrom as a result of said phase change, wherein said phase change creating means includes a means to change a pressure within said container, wherein said phase change means includes a means to change a temperature of the blood product, wherein said temperature change means includes a heat transfer fluid having a temperature distinct from a temperature of the blood product, said heat transfer fluid juxtaposed adjacent an exterior of said container such that heat transfer occurs between said heat transfer fluid and the blood product until a phase change occurs in the blood product, and wherein said apparatus includes a means to spray said heat transfer fluid against said exterior of said container, whereby said heat transfer fluid is caused to reside adjacent said container for a period of time less than all of the time said spray means is in operation such that a temperature differential between said heat transfer fluid and the blood product is maximized.

* * * * *